(12) United States Patent
Wada et al.

(10) Patent No.: US 7,274,829 B2
(45) Date of Patent: Sep. 25, 2007

(54) MEASURING METHOD AND INSTRUMENT COMPRISING IMAGE SENSOR

(75) Inventors: Atsusi Wada, Kyoto (JP); Kouji Egawa, Kyoto (JP)

(73) Assignee: Arkray, Inc., Kyoto (JP)

( * ) Notice: Subject to any disclaimer, the term of this patent is extended or adjusted under 35 U.S.C. 154(b) by 883 days.

(21) Appl. No.: 10/415,986

(22) PCT Filed: Nov. 9, 2001

(86) PCT No.: PCT/JP01/09851

§ 371 (c)(1),
(2), (4) Date: May 6, 2003

(87) PCT Pub. No.: WO02/39094

PCT Pub. Date: May 16, 2002

(65) Prior Publication Data

US 2004/0076325 A1   Apr. 22, 2004

(30) Foreign Application Priority Data

Nov. 10, 2000 (JP) ............................. 2000-343366

(51) Int. Cl.
*G06K 9/40* (2006.01)
(52) U.S. Cl. .................................................... 382/274
(58) Field of Classification Search ................ 382/254, 382/274, 312, 321
See application file for complete search history.

(56) References Cited

U.S. PATENT DOCUMENTS 5,592,218 A * 1/1997 Ochiai et al. ................ 348/110

(Continued)

FOREIGN PATENT DOCUMENTS

| EP | 0 440 443 A2 | 8/1991 |
|----|----|----|
| EP | 0 657 730 A1 | 6/1995 |
| JP | 51-26595 A1 | 3/1976 |
| JP | 58-3680 A1 | 6/1981 |
| JP | 60-11140 A1 | 1/1985 |

(Continued)

OTHER PUBLICATIONS

English Translation of Japanese Patent No. 03-289777, entitled "Infrared Image Pickup Device" pp. 1-13, Dec. 19, 1991.*

(Continued)

*Primary Examiner*—Daniel Miriam
(74) *Attorney, Agent, or Firm*—Rader, Fishman & Grauer PLLC

(57) ABSTRACT

A linearizing correction unit (104) carries out a linearizing correction process on the output of an image sensor (8) based upon linearizing correction data stored in a linearizing correction data holding unit (102), and a light-irregularity correction unit (108) carries out a light-irregularity correction process on the image sensor output that has been subjected to the linearizing correction process based upon light-irregularity correction data stored in a light-irregularity correction data holding unit (106). A refection factor calculation unit (110) calculates an integral value of the in-plane reflection factor of a test piece by using the output that has been subjected to the linearizing correction and light-irregularity correction with respect to pixel outputs of the image sensor (8) obtained when the test piece having in-plane density irregularities is measured. A quantifying unit (114) applies calibration curve data of a calibration-curve-data holding unit (112) to the integrated reflection factor obtained by the reflection factor calculation unit so that a sample density of the test piece is calculated.

25 Claims, 33 Drawing Sheets

U.S. PATENT DOCUMENTS 6,075,605 A * 6/2000 Futamura et al. ............ 356/608
6,075,903 A * 6/2000 Breiter et al. ................ 382/261
6,175,649 B1 * 1/2001 Kiyohara et al. ............ 382/167

FOREIGN PATENT DOCUMENTS

| JP | 60-105935 | A1 | 6/1985 |
| JP | 62-294940 | A1 | 12/1987 |
| JP | 64-32149 | A1 | 2/1989 |
| JP | 03-289777 | * | 12/1991 |
| JP | 03-296037 | A1 | 12/1991 |
| JP | 06-50814 | A1 | 2/1994 |
| JP | 07-253398 | A1 | 10/1995 |

OTHER PUBLICATIONS

International Search Report for PCT/JP01/09851 mailed on Dec. 11, 2001.

International Preliminary Examination Report completed on Dec. 10, 2002.

* cited by examiner

MEASURING METHOD AND INSTRUMENT COMPRISING IMAGE SENSOR

FIELD OF THE INVENTION

The present invention relates to a measuring method which applies light to a measuring object such as a test piece and carries out measurements two-dimensionally or along a straight line, by receiving light reflected from the test piece by an image sensor such as an area sensor and an image scanner, a measuring method for a measuring object which obtains a sample density of a detected portion based upon the measured value, and a device for achieving such a method.

In the present invention, the light to be measured includes various kinds of light, such as reflected light, transmitted light, fluorescent light, phosphor light and chemically emitted light, which are used in quantitative measurements and qualitative measurements.

BACKGROUND OF THE INVENTION

Photodetectors include a photodetector element constituted by single elements such as a photodiode, a linear sensor constituted by photodetector elements that are aligned on a line, such as a photodiode array, and an image sensor constituted by photodetector elements that are arranged two-dimensionally, such as a CCD (charge-coupled device) sensor and a CMOS sensor.

With respect to a sensor for use in a measuring device, which measures light from a measuring object, a photodiode has been mainly used from the viewpoint of superior precision, cost performance and technical easiness. However, in an attempt to obtain reflection factors or the like of a plurality of items by using the photodiode, an optical system or a test piece needs to be shifted.

Moreover, since the photodiode is used for obtaining data that is averaged within a spot diameter, it is not suitable for use in precisely detecting color developments, as typically exemplified by detection of spot color developments.

With respect to an immuno-chromatograph test piece measuring device, only the device of a driving photometric type that measures light with an optical system being shifted on a test piece has been proposed.

In order to solve these problems, the application of an image sensor is proposed. Since data of the image sensor is image information relating to a target area, measurements of a plurality of items, detection of spot color developments, correction of positional deviations in test pieces, etc. may be carried out based upon information of one frame.

Detections of the shape and color of a subject by the use of an image sensor have been well-known. For example, a method in which an image of a test strip for use in immunization measurements is picked up by a CCD camera so that determination is made based upon the area or the ratio of the longitudinal and lateral lengths has been proposed (see Japanese Patent Application Laid-Open No. 9-257708). In this method, after the picked-up signal has been binarized as a luminance signal, the shape of an image is measured; therefore, this method is not used for measuring the density within the image.

With respect to another example in which two-dimensional measurements are carried out by using an image sensor, an urine measuring device is listed. In this device, in general, measurements are carried out by determining not the density (brightness) in color developments, but the color gradation (hue) in urine test paper, and a color-CCD device is used.

In an attempt to detect a two-dimensional density distribution of a test piece with high precision by using an image sensor, in addition to irradiation irregularities in light, lens aberration, etc., in-plane light irregularities occur due to a sensitivity difference between pixels of the image sensor. For this reason, in order to carry out detections with high precision, in general, the sensor or the measuring object is shifted by using a mechanical driving system. In such a case, even if the image sensor is applied, it is merely utilized as a one-dimensional linear sensor.

It has not been clarified whether or not the reflection factor or the like can be measured two-dimensionally by using an image sensor such as a CCD sensor and a CMOS sensor.

Therefore, the first objective of the present invention is to provide a measuring method, which makes it possible to measure light from a measuring object two-dimensionally or along a straight line by using an image sensor, and a device for use in such a method.

Moreover, the second objective of the present invention is to achieve a measuring method for a measuring object, which uses an image sensor as a detection device, and carries out quantitative measurements on the measuring object such as an immuno-chromatograph test piece based upon measurements of light from the measuring object, and a device for use in such a method.

DISCLOSURE OF THE INVENTION

In order to achieve the first objective, the measuring method of the present invention features that light from a measuring object is received by an image sensor so as to carry out a pre-process on the output of each pixel in the image sensor, and that an integral value is calculated from the pixel output that has been subjected to the pre-process. The pre-process of the pixel output includes a linearizing correction process for correcting an output of the image sensor so as to make the output of the image sensor proportional to the quantity of incident light, and a light-irregularity correction process which corrects respective pixel outputs so that, upon measuring a reference object, the respective pixel outputs of the image sensor that have been subjected to the linearizing correction are made even.

With respect to the reference object, for example, a reflection plate having even in-plane density or a blank state (a state in which all the measuring light is made incident on an image sensor without placing a measuring object) is prepared.

With this arrangement, it becomes possible to easily measure the reflection factor two-dimensionally or along a straight line.

In the case when the detection range is fixed to only the color-developing area, positional deviations of the measuring object give adverse effects to the detection intensity. Moreover, if the intensity and area of the measuring object vary after the color development, deviations become greater in the measuring results.

Here, with respect to a desirable method for obtaining an integral value of light from the color-developing area of the measuring object, after measurements have been carried out on an area greater than the color-developing area with a non-color-developing area being included therein, an integral value of light from the color-developing area is obtained. With respect to the method, a straight line connecting the pixel outputs of two points sandwiching the color-developing area of the measuring object is set as a baseline value of the pixel output, and based upon a value obtained by converting the pixel output corresponding to each of the positions of the measuring object using the baseline value, the integral value is preferably obtained.

In accordance with the integral value calculation method of light from the measuring object, calculations are carried out with the non-color-developing area of the measuring object being included therein, and the intensity of the color-developing area is not impaired. Even in the case when the position of the measuring object is deviated slightly, as long as the color-developing area is located within the detection range, it is possible to avoid influences to the calculation results.

Moreover, since the straight line connecting the pixel outputs of two points sandwiching the color-developing area of the measuring object, that is, a straight line connecting the pixel outputs of non-color-developing portions at both of the ends of the light-developing area, is set to a baseline value, it is possible to reduce variations in the intensity due to coloring of the measuring object as well as variations in the intensity due to the height and gradient of the measuring object.

Consequently, even when the color-developing intensity and area of the measuring object are varied, it is possible to prevent the variations from causing adverse effects on the calculation results.

In accordance with a first aspect, the linearizing correction of the pre-process includes the following processes (A) and (B):

(A) A process in which: a photodetector having linearity in its output in response to the quantity of received light is arranged so that light to be made incident on the above-mentioned image sensor is simultaneously made incident on the photodetector, and upon variation in the quantity of incident light, the relationship between the image sensor output and the output of the above-mentioned photodetector is stored as linearizing data; and (B) A process in which, upon measurement of a measuring object, the resulting image sensor output is corrected and made proportional to the output of the photodetector based upon the linearizing data.

In accordance with a second aspect, the linearizing correction of the pre-process includes the following processes (A) and (B):

(A) A process in which: a plurality of standard plates which generate mutually different light rays that have been known are prepared, and after measuring each of these standard plates, the relationship between the image sensor output and light from each of the standard plates is stored as linearizing data; and (B) A process in which the image sensor output obtained upon measuring a measuring object is corrected so as to be made proportional to light from the standard plate based upon the linearizing data.

In accordance with a third aspect, the linearizing correction of the pre-process includes the following processes (A) and (B):

(A) A process in which: the above-mentioned image sensor is allowed to variably set exposing time, and upon measuring one reference object, the relationship between each of sensor outputs obtained from measurements carried out while changing the exposing time in a plurality of stages and the corresponding exposing time is stored as linearizing data relating to light from the reference object, which is proportional to the exposing time, and (B) A process in which: the image sensor output, obtained upon measuring a measuring object, is corrected so as to be made proportional to light from the reference object that is obtained by the exposing time based upon the linearizing data.

A measuring device to be used for carrying out the measuring method of the present invention is provided with an image sensor which receives light from a measuring object and a calculation unit which calculates an integral value of light from the in-plane of a measuring object by using respective pixel outputs of the image sensor.

In order to achieve the second objective, the measuring method for a measuring object in the present invention calculates the sample density of the measuring object by applying calibration curve data that represents the relationship between the integral value and the sample density of the measuring object to the integral value.

With this arrangement, it becomes possible to easily carry out the density measurement of the measuring object such as an immuno-chromatograph test piece.

In order to carry out the measuring method for a measuring object in the present invention, a measuring-object measuring device, which relates to the measuring device of the present invention, is further provided with: a calibration-curve holding unit that holds the relationship between the integral value of light from the measuring object and the sample density of the measuring object; and a quantifying unit which applies the calibration-curve data of the calibration-curve holding unit to the integral value of light from the measuring object that has been obtained in the calculation unit to calculate the sample density of the measuring object.

BRIEF DESCRIPTION OF THE DRAWINGS

FIG. 4 shows specific examples of optical systems in the above-mentioned embodiment.

FIG. 9 is a drawing that shows one example of a correcting process.

FIG. 8 is a plan view that shows pixel positions that are subjected to light-irregularity corrections.

BEST MODE FOR CARRYING OUT THE INVENTION

In an attempt to carry out quantitative measurements by using an image sensor based upon reflection factors and the like, the following problems are raised:

(1) The output characteristics of a pixel in a linear sensor with respect to the quantity of light do not exhibit linearity like that of a photodiode, and has an S-letter-shaped sensitivity characteristics that are out of a straight line in areas having a small quantity of light and a large quantity of light For this reason, it has been considered that the linear sensor is not suitable for quantitative measurements.

(2) In an attempt to carry out two-dimensional or one-dimensional measurements, in-plane light irregularities occur due to irradiation irregularities in light, lens aberration, etc., and deviations in pixel sensitivity depending on positions; consequently, positional deviations occur in the results of the quantitative measurements.

Therefore, it is desirable to solve these problems that occur in the case when an image sensor is used as the detector in an attempt to achieve a convenient two-dimensional measuring device without the necessity of a mechanical driving system.

The following description will exemplify a case in which a reflection factor is measured; however, not limited to the reflection factor, the present invention may also be applied to measurements of such as transmittance, fluorescent light and chemically emitted light, in the same manner.

Figure 1:
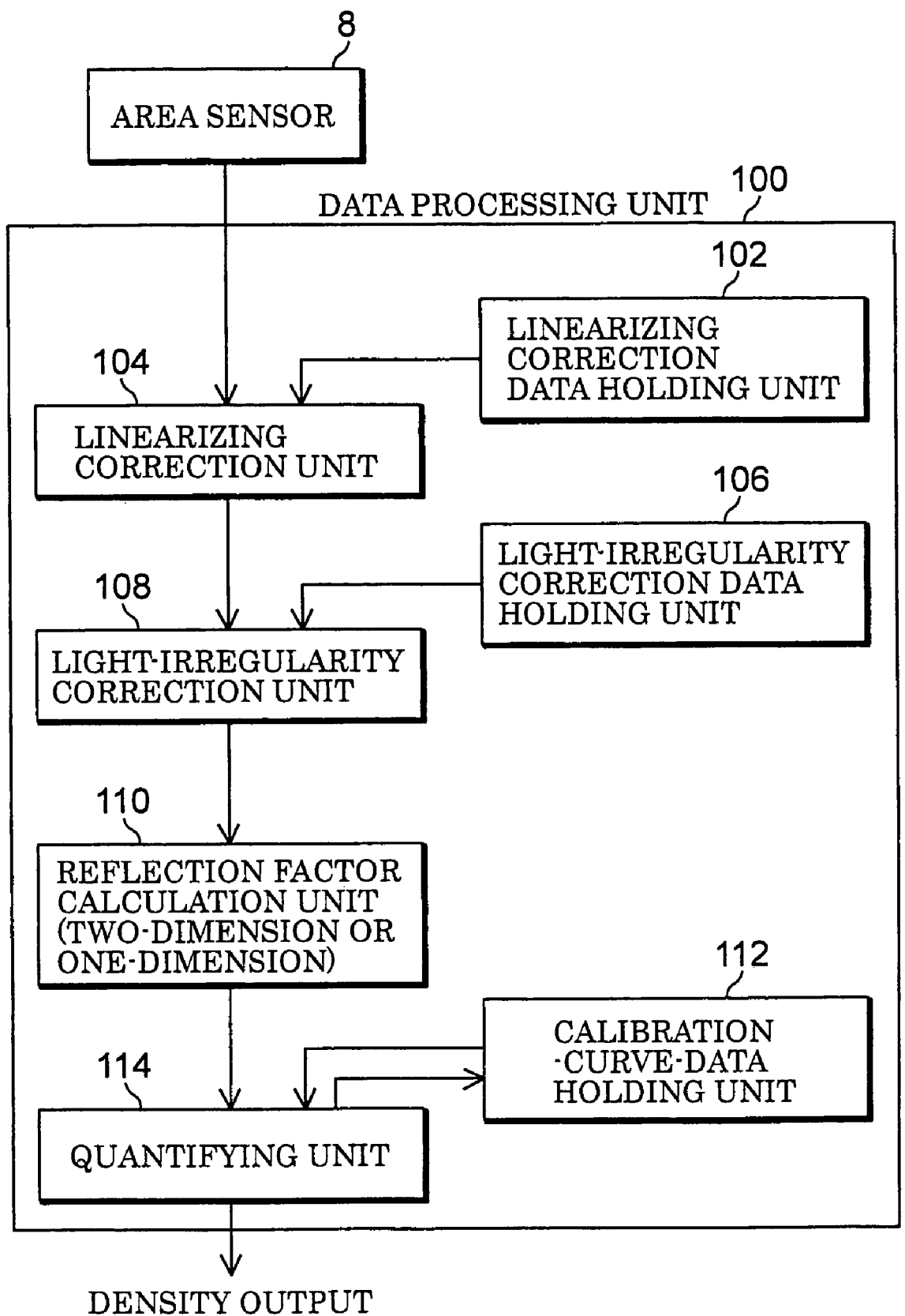
FIG. 1 is a block diagram that schematically shows one embodiment of the present invention.

FIG. 1 schematically shows an embodiment in which the present invention is applied to a reflection-factor measuring device.

This reflection-factor measuring device is provided with a sample base on which a test piece is placed, a light source which applies light to the test piece placed on the sample base, an area sensor 8 that receives reflected light from the test piece placed on the sample base, a linearizing correction data holding unit 102 that holds linearizing correction data used for correcting the output of the image sensor so as to make the output of the area sensor 8 proportional to the quantity of incident light, a linearizing correction unit 104 which corrects to linearize the output of the area sensor 8 based upon the linearizing correction data held on the linearizing correction data holding unit 102, a light-irregularity correction data holding unit 106 for holding light-irregularity correction data which, when a flat plate having even in-plane density is measured as the test piece, allows the resulting output of each pixel of the area sensor 8 that has been corrected by using the linearizing correction data to be made even, a light-irregularity correction unit 108 which carries out light-irregularity correcting processes on the image sensor output that has been subjected to the linearizing correction based upon the light-irregularity correction data held in the light-irregularity correction data holding unit 106, and a reflection factor calculation unit 110 which calculates an integral value of an in-plane reflection factor of an unknown test piece having in-plane density irregularities by using the output that has been subjected to the linearizing correction and the light-irregularity correction with respect to each of pixel outputs of the area sensor 8 upon measurements of the unknown test piece.

The linearizing correction unit 104 carries out linearizing correction processes on the output of the area sensor 8 based upon the linearizing correction data held on the linearizing correction data holding unit 102. The light-irregularity correction unit 108 corrects light irregularities of the image sensor output that has been subjected to the linearizing correction, based upon the light-irregularity correction data held in the light-irregularity correction data holding unit 106. With each of pixel outputs of the area sensor 8 upon measurements of a test piece having in-plane density irregularities, the reflection factor calculation unit 110 calculates an integral value of the in-plane reflection factor of the test piece by using the output that has been subjected to the linearizing correction and the light-irregularity correction.

Raw image information, picked up by using this reflection-factor measuring device, causes light irregularities due to influences from individual differences in sensitivity of the respective pixels in the area sensor 8, irradiation irregularities of the LEDs 4, cosine quadruple rule (aberration) of the lens 6 and the like. "Light irregularities" are resulted from all these influences.

In addition to the above-mentioned reflection-factor measuring device, a test-piece measuring device is further provided with a calibration-curve data holding unit 112 which stores the relationship between the reflection factor and the sample density of a test piece, and a quantifying unit 114 which applies the calibration-curve data of the calibration-curve data holding unit 112 to an integrated reflection factor obtained by the reflection factor calculation unit to calculate the sample density of a measured test piece.

With respect to the calibration-curve data held by the calibration-curve data holding unit 112, those data obtained by another test-piece measuring device may be used; however, from the viewpoint of the sensitivity characteristics of the image sensor, light irregularities and the like, the standard sample is preferably measured by a test-piece measuring device itself to be used so that the calibration-curve data is formed in its quantifying unit so as to be stored in the calibration-curve data holding unit 112.

In the present embodiment, after light has been applied to a test piece and the light reflected from the detection subject portion has been received by the area sensor 8, the following (A) linearizing correction process and (B) light-irregularity correction process are executed to correct the output of the area sensor 8.

(A) In the linearizing correction process in the linearizing correction unit 104, based upon the linearizing correction data held in the linearizing correction data holding unit 102, the output of the area sensor 8 is corrected so that upon variation in the quantity of light, the output of the area sensor 8 is made proportional to the quantity of light.

(B) In the light-irregularity correction process in the light-irregularity correction unit 108, the output of each pixel is corrected so that, when a flat plate having even in-plane density is measured as the test peace, the resulting output of each pixel of the area sensor 8 that has been corrected by using the linearizing correction data is made even.

The output from the image sensor and the output from the photodetector are preferably set as values that have been subjected to offset processes in which the output when the quantity of light is zero is subtracted from these outputs as dark data.

In accordance with the present embodiment, the output from the area sensor 8 is allowed to have linearity based upon the linearizing correction, and becomes free from light irregularities within the measuring face thereof through the light-irregularity correction; therefore, it becomes possible to carry out reflection factor measurements with high precision two-dimensionally or along a straight line within the face of the test piece without the necessity of any mechanical driving system.

Thus, based upon the resulting reflection factor, it becomes possible to appropriately quantify the sample density of the test piece.

EMBODIMENT 1

With respect to the first embodiment, the following description will discuss a two-dimensional reflection factor measuring device in which an area sensor is used as a sensor and to which the output correcting method in accordance with the first aspect of the present invention is applied.

Figure 2:
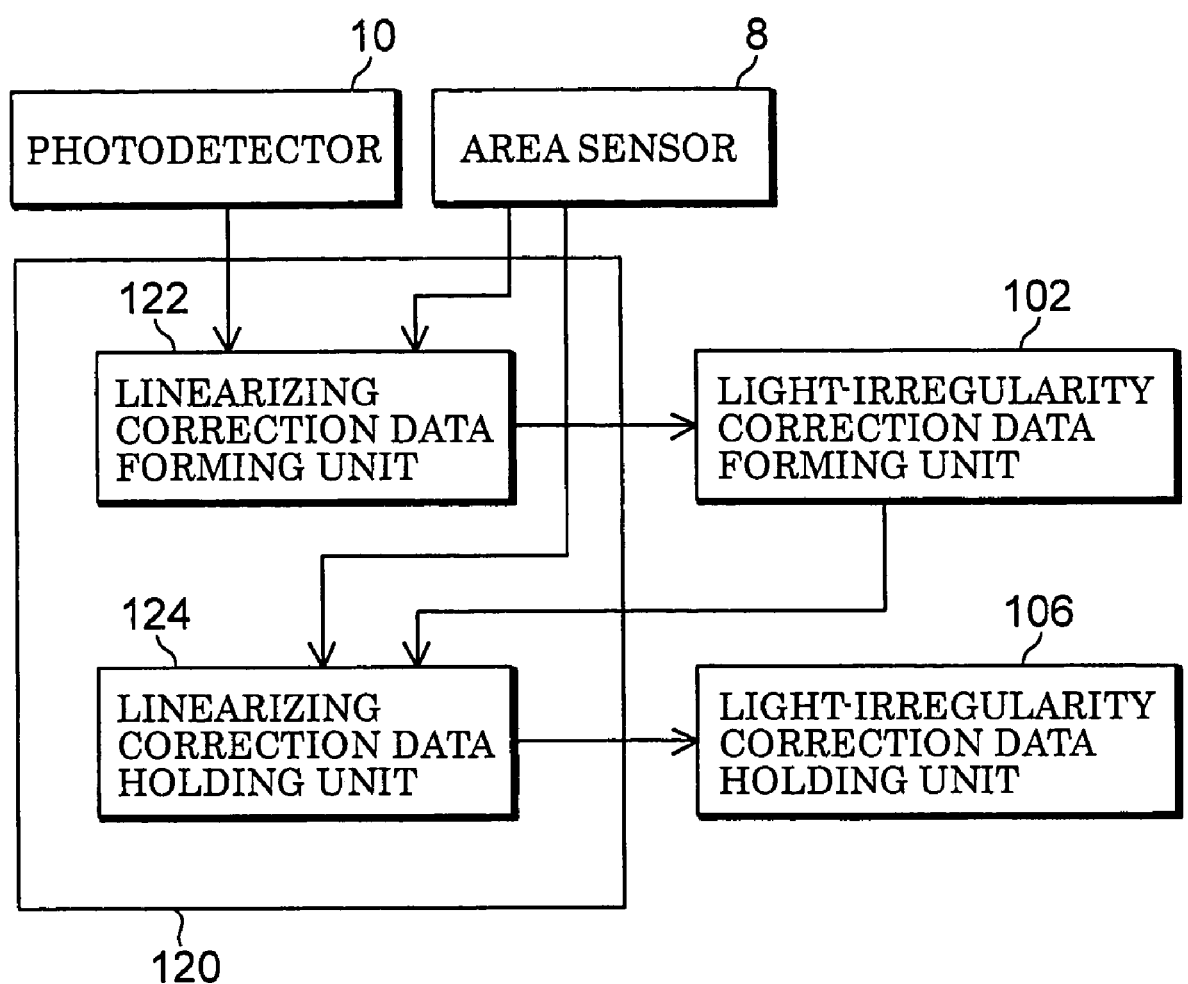
FIG. 2 is a block diagram that schematically shows a preferred mode of the present invention.

The linearizing correction data held in the linearizing correction data holding unit 102 and the light-irregularity correction data held in the light-irregularity correction data holding unit 106 may be generated by this reflection-factor measuring device or a test-piece measuring device. Therefore, as shown in FIG. 2, the measuring device is preferably further provided with a photodetector 10 which is placed at a position for receiving light reflected from a test piece held on a sample base, and has an output that has linearity with respect to the quantity of light to be received; a linearizing correction data forming unit 122 which forms linearizing correction data that is used for correcting the output of the area sensor 8 in such a manner that, upon variation in the quantity of light from a light source, the output of the area sensor 8 is made proportional to the output of the photodetector 10, and allows the linearizing correction data holding unit 102 to store the resulting data; and a light-irregularity data forming unit 124 which forms light-irregularity correction data that corrects respective pixel outputs so that, upon measuring a flat plate having even in-plane density as a test piece, the respective pixel outputs of the area sensor 8 that have been subjected to the linearizing correction are made even, and stores the resulting data in the light-irregularity correction data holding unit 106.

For example, the linearizing correction data forming unit 122 has an arrangement in which, a white plate is measured as a test piece, and some pixels in the vicinity of the brightest pixel within an image are selected so that by using the average value of these pixel outputs, linearizing correction data is formed.

For example, the light-irregularity correction data forming unit 124 has an arrangement in which, a white plate is measured as a test piece, and light-irregularity correction data is formed with respect to image data corresponding to the quantity of light having a fixed rate to the quantity of light when the pixel has reached the saturated quantity of light Here, with respect to the area sensor 8, for example, a CCD or CMOS sensor may be used.

With respect to the photodetector 10 whose output has linearity with respect to the quantity of light to be received, for example, a photodiode may be used.

The reflection factor calculation unit 110 executes an integration process on the reflection factor two-dimensionally within the face of the test piece or along a straight line within the face of the test piece.

Figure 3:
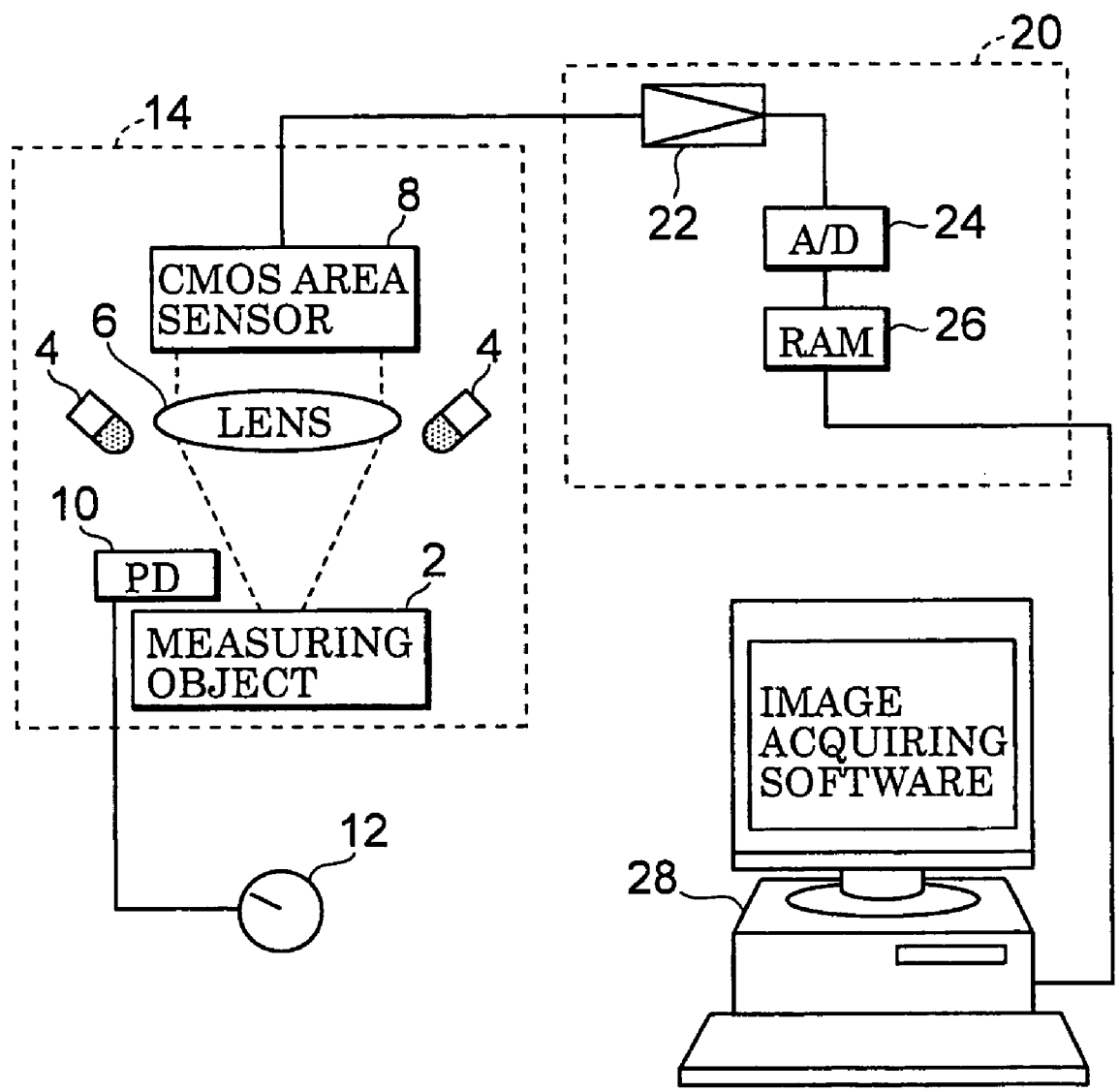
FIG. 3 is a structural drawing that shows one embodiment of the present invention as a partial block diagram.

FIG. 3 schematically shows the reflection-factor measuring device of the present embodiment including an optical system.

Reference numeral 2 represents a test piece serving as a measuring object, which is held on a sample base (not shown in Figures), and placed at a predetermined position. Upon actual measurements such as a clinical inspection, the test piece 2 is test paper such as urine test paper and immunization measuring-use test paper, and a thin-film chromatograph in a, chemical analysis; however, in the case when an image sensor is corrected, a white plate having even reflection factor on the surface is used as the measuring object In order to irradiate the test piece 2, three LEDs (light-emitting diodes) 4 serving as light sources are placed above the periphery of the test piece 2 at the same level with 120-degree intervals from each other so as to apply a light beam to the test piece 2 with an incident angle of 45 degrees toward the center of the test piece 2. Each of the LEDs 4 has a center wavelength of 635 nm in its light emission.

A CMOS area sensor 8is placed above the test piece 2 through an image-converging lens 6. In this embodiment, a CMOS area sensor is used as the image sensor. Reflected light from the test piece 2 is converged to form an image on the area sensor 8 by the lens 6 so that image information of the test piece 2 is detected by the area sensor 8.

A photodetector (PD) 10 is placed at a position out of the image angle of the area sensor 8 from which the quantity of light from the LEDs 4 is sensed. The photodetector 10 is prepared as a photodiode, and its output has linearity with respect to the quantity of received light, and converts the quantity of irradiated light applied to the test piece 2 into a voltage. Reference numeral 12 is a voltmeter that converts the quantity of light received by the photodetector 10 into a voltage.

A broken-line block 14 represents the fact that the LEDs 4, the lens 6, the area sensor 8 and the photodetector 10 constitute an optical system of this reflection-factor measuring device.

A broken-line block 20 represents an area sensor drive circuit, and is provided with an amplifier 24 for amplifying an output of the area sensor 8, an A/D converter 24 for converting an amplified analog output to a digital signal, and a RAM (random-access-memory) 26 for temporarily holding an acquired digital signal. This area sensor drive circuit 20 controls the area sensor 8 so as to set a register for image-pickup time and to acquire image data and the like. Moreover, the area sensor drive circuit 20 adjusts the quantity of light from the LEDs 4, carries out serial communications (56000 bps) with a personal computer 28, and executes instructions from the personal computer 28.

The personal computer 28 carries out various register settings of the area sensor 8, gives instructions to the area sensor drive circuit 20, acquires image information, and displays the image on a monitor. Moreover, it stores data in an appropriate format The personal computer 28 also achieves functions of various units included in the data processing unit 100 surrounded by a frame 100 in FIG. 1 and of various units included in the correction data forming unit 120 surrounded by a frame 120 of FIG. 2.

Figure 4A:
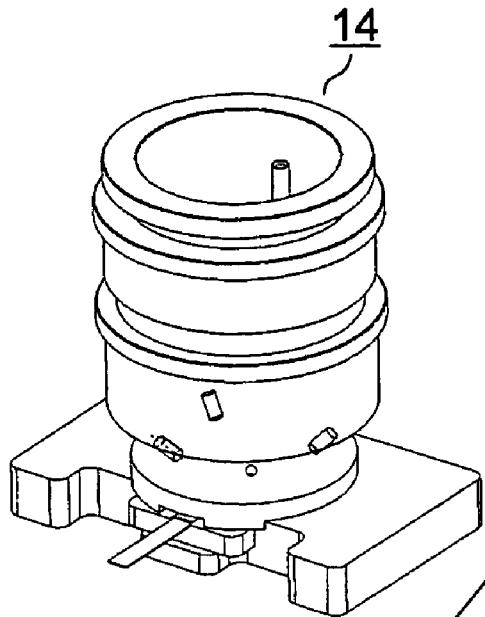
FIG. 4(a) shows an outside view of the optical system.
Figure 4B:
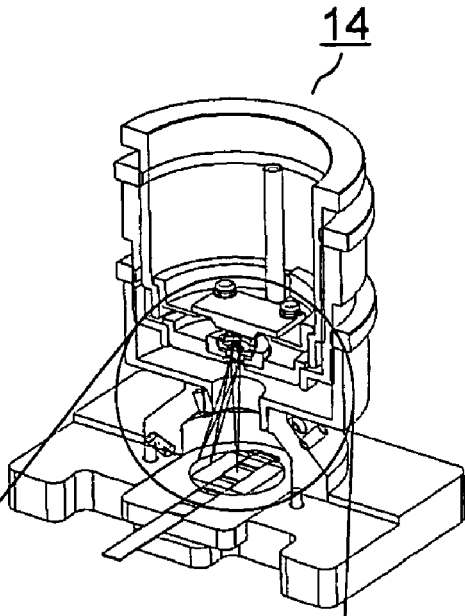
FIG. 4(b) shows a longitudinal cross-sectional view thereof.
Figure 4C:
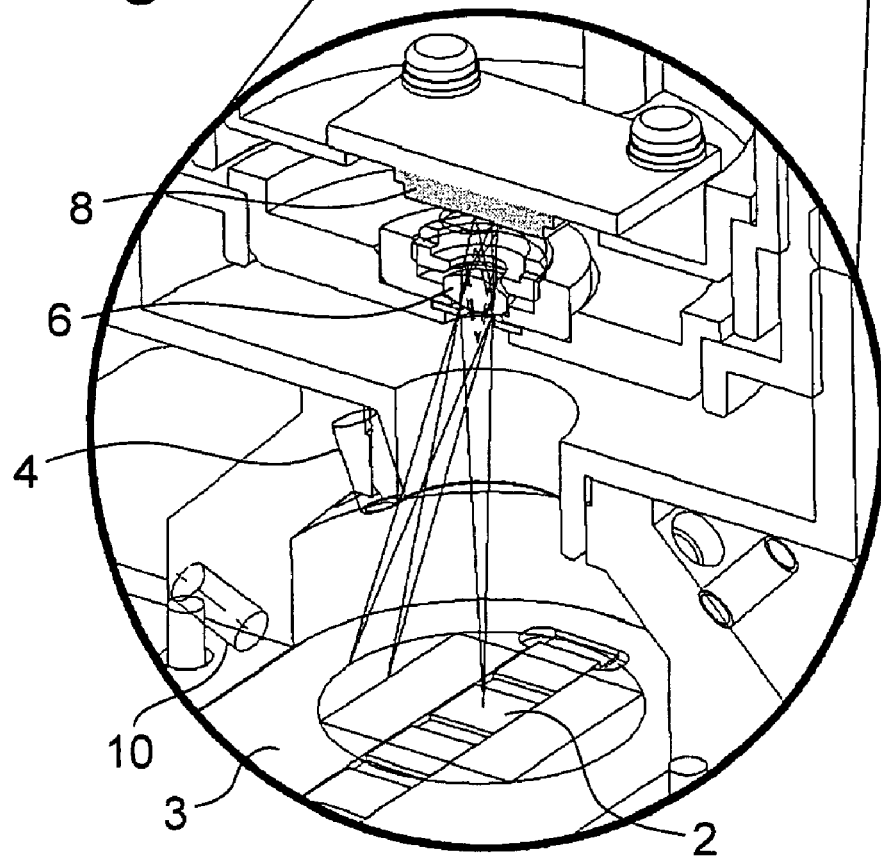
FIG. 4(c) shows an enlarged view within the circle in FIG. 4(b).

FIG. 4 shows a specific example of an optical system 14. FIG. 4(*a*) shows an outside view of the optical system, FIG. 4(*b*) shows a longitudinal cross-sectional view thereof, and FIG. 4(*c*) shows an enlarged view within the circle in FIG. 4(*b*).

This optical system has an arrangement in which the distance from the lens 6 to the test piece 2 and the distance from the lens 6 to the area sensor 8 are finely adjusted freely; thus, it is possible to easily carry out a focusing process and a magnification-changing process. Moreover, the test piece 2 can be exchanged together with a base plate 3 of the sample base.

Reflection-factor measurements were carried out by using a CMOS image sensor (H64283FP) made by Mitsubishi Electric Corporation as the area sensor 8, and the following description will discuss the results of the measurements.

First, the following description will explain the correction process of the area sensor 8.

(1) Offset Process (Dark Process)

Supposing that the current value of the LEDs 4 is 0 (mA), the output (A/D count value) of the area sensor 8 at this time is defined as a dark (offset) state. With respect to all the calculation results (correction processes, reflection factor calculations and the like), which will be described below, a difference between the output (A/D count value) of the area sensor 8 upon irradiation by the LEDs 4 and the dark level is defined as the original output (A/D count value) of the area sensor 8.

(2) Relationship between the Quantity of Light and the Image Sensor Output (Linearizing Correction):

The relationship between the quantity of light emitted by the LEDs 4 to the test piece 2 and the output of the area sensor 8 (count value obtained by A/D converting Vout) is not a directly proportional relationship.

Figure 5:
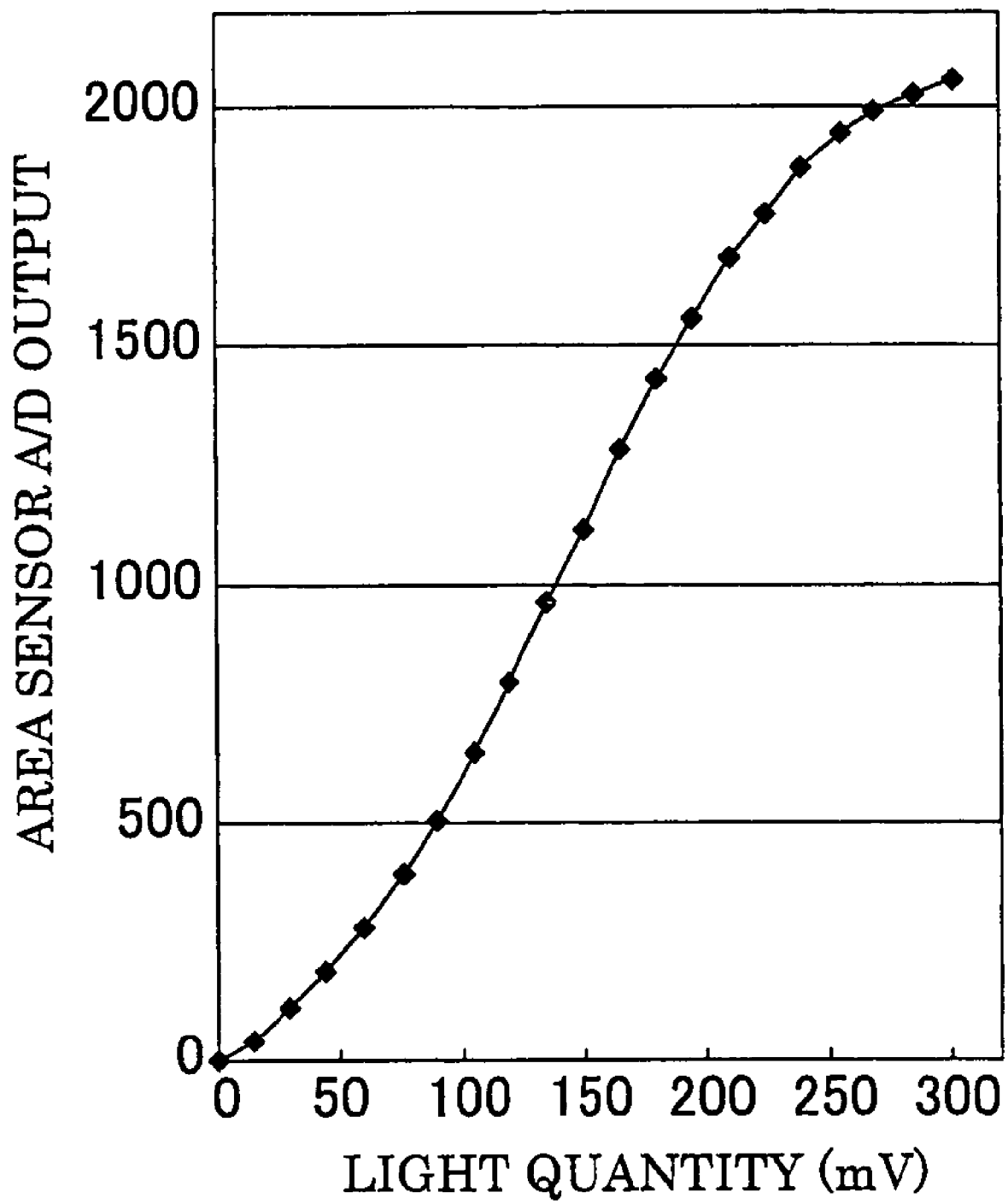
FIG. 5 is a drawing that shows the output characteristics of an area sensor.

A graph shown in FIG. 5 shows the output of the area sensor 8 obtained by varying the quantity of light from the LEDs 4, while a white plate (ND (neutral density): 9.5, actual value of reflection factor 87.00% (the actual value of reflection factor is measured by a spectrophotometer (MINOLTA CM-503c)(the same is true for the following measurements))) is used as the test piece 2. The axis of abscissas indicates the output (mV) of a photodetector 10 placed within the optical system 14, and the axis of ordinates indicates the average value of data of appropriate 5 pixels that are successively aligned at a portion of the area sensor 8 that receives the strongest light.

In order to correct light irregularities, it is necessary to carry out processes for converting the output (A/D count value) of the area sensor 8 to the output (mV) of the photodetector 10 as pre-processes. Prior to the light irregularity correction, characteristics shown in FIG. 5 are measured under the condition of 25° C., and based upon the results of the measurements, the output of each pixel of the area sensor 8 is corrected and calculated.

Figure 6:
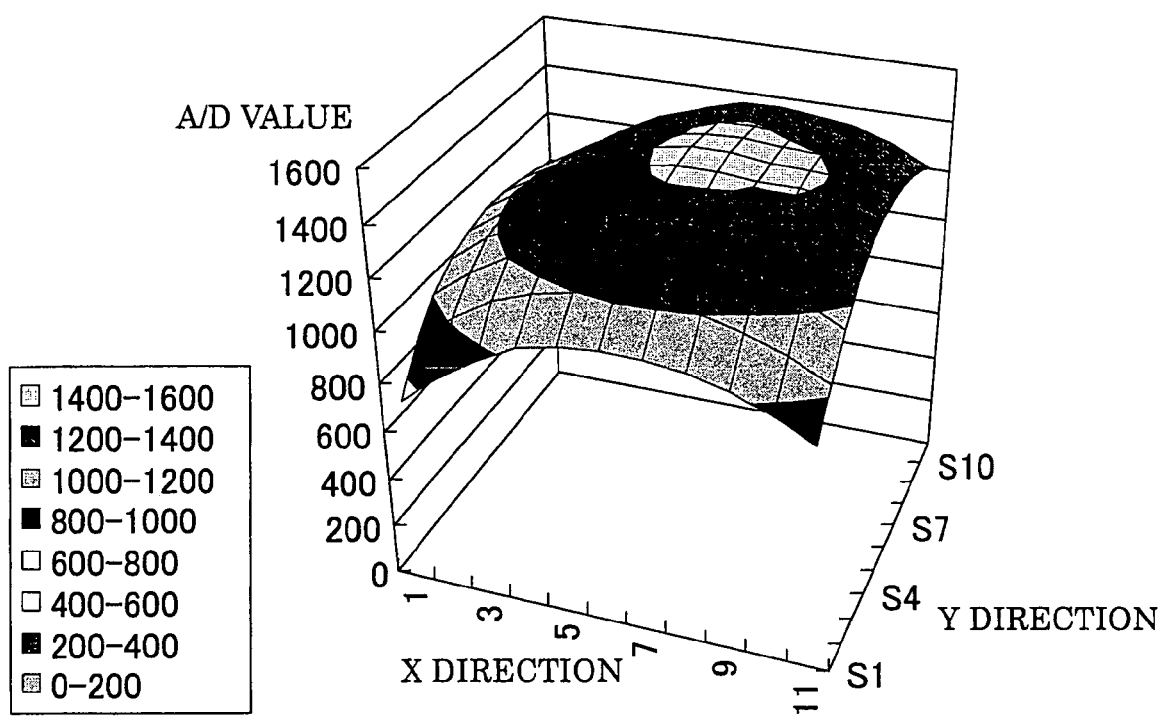
FIG. 6 is a three-dimensional contour face graph obtained when an image of a white plate is picked up by an area sensor.

(3) Image Irregularity (Light Irregularity) Correction:

The raw image information, picked up by using this reflection-factor measuring device, causes light irregularities due to influences from individual differences in sensitivity of the respective pixels in the area sensor 8, irradiation irregularities of the LEDs 4, cosine quadruple rule (aberration) of the lens 6 and the like. In FIG. 6, an image of a white plate (ND: 9.5, actual value of reflection factor: 87.00%)(all the image angle range is occupied by the white plate area) is picked up, and the image information is indicated by a three-dimensional contour face graph. The contour face is formed by dividing the image into 10×10 areas and using the average value of pixels contained in each of the areas.

The graph of FIG. 6 shows that, even in the case when an image of a flat face having even density, such as a white plate, is picked up, density information within the image angle is deformed into a dome shape due to influences from light irregularities. Processes for correcting such image information deformed into the dome shape to a horizontal face having even density are essential to a case in which the area sensor 8 is used as the photodetector in the reflection-factor measuring device. In the present invention, all the results of measurements are obtained by carrying out this light irregularity correction.

Figure 7:
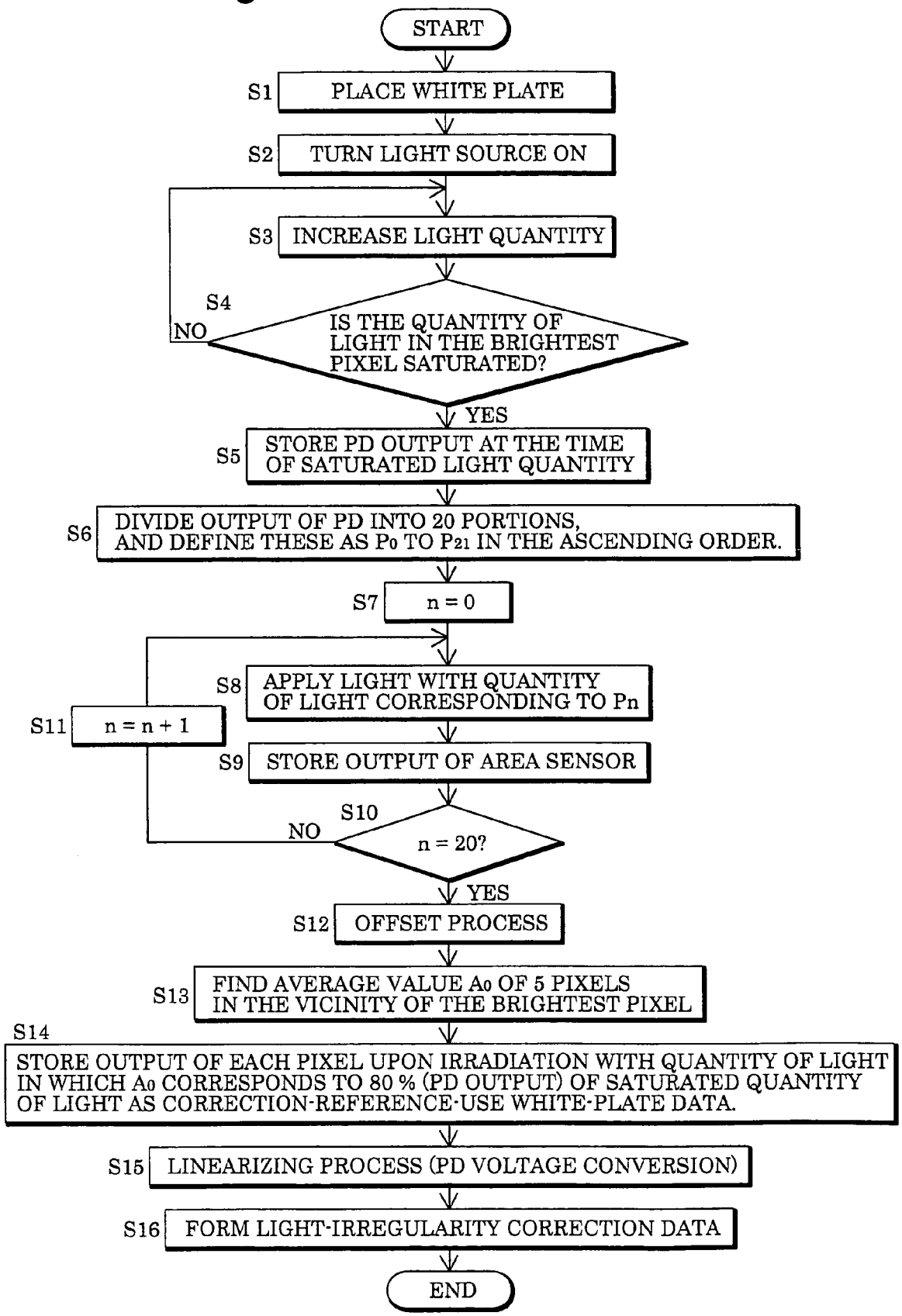
FIG. 7 is a flow chart that shows one example of a correction process of the present invention.

In the present invention, the correction processes were carried out in accordance with the following sequence. Referring to FIG. 7, the sequence will be explained.

<Acquiring Sequence for Correction Reference Data>

(1) A white plate (ND: 9.5, actual value of reflection factor. 87.00%) is used as the test piece 2 so that a voltage value of the photodetector (PD) 10 is obtained when the brightest pixel within the picked-up image has reached the saturated quantity of light (steps S1 to S5).

(2) The voltage value of the photodetector 10 obtained when the pixel has reached the saturated quantity of light from 0 (mV) is divided into 20 equal portions so that respective voltage values of 21 stages are obtained, and these are indicated as P0 to P21 in the ascending order (step S6).

(3) The quantity of light of the LEDs 4 is adjusted so that voltage values of the photodetector 10 are set to the respective stages. Images of the white plate are picked up by using the respective quantities of light, and the pieces of corresponding data are stored (21 sheets of image data are obtained. The image corresponding to 0 (mV) is referred to as dark data.) (steps S7 to S11).

(4) All the pieces of image data are subjected to offsetting processes (that is, the value of the dark data is subtracted from each piece of image data for each pixel) (step S12).

(5) Five pixels that are successively aligned in the vicinity of the brightest pixel within the image are averaged. These processes are carried out on each image so that the relationship (see FIG. 5) between the voltage value of the photodetector 10 and the output of the image sensor is obtained (step S13).

This relationship is stored in a linearizing correction data storing unit 102 as linearizing correction data.

(6) Among 21 sheets of image data, the image data corresponding to the saturated quantity of light ×0.8 is selected as light-irregularity correction-reference-use white plate data (step S14).

<Light-Irregularity Correction Sequence of Measured Image>

(7) A/D data corresponding to each of 128×128 pixels of a measured image is converted to a voltage value of the photodetector 10 based upon the relationship shown in FIG. 5 (PD voltage-value conversion: linearizing process), which has been stored in the linearizing correction data storing unit 102 (step S15). The conversion is carried out by linearly interpolating gaps between sample points in the graph of FIG. 5.

(8) With respect to the light-irregularity correction-reference-use white plate data obtained in the process (6), the PD voltage value conversion is carried out in the same manner.

(9) The ratio of the measured image data (after the PD voltage-value conversion) to the light-irregularity correction-reference-use white plate data (after the PD voltage-value conversion) is obtained for each of 128×128 pixels. This ratio is set as light-irregularity correction data, and stored in a light-irregularity correction data holding unit 106 (step S16).

(Example of Pixel Correction)

The following description will explain an example in which the quantity of reflected light is obtained from the resulting output from each of the pixels by using the above-mentioned correction method. Pixels to be corrected are five points shown in FIG. 8, which are respectively set to point 1 (32, 32), point 2 (96, 32), point 3 (64, 64), point 4 (32, 96) and point 5 (96, 96).

Figure 8:
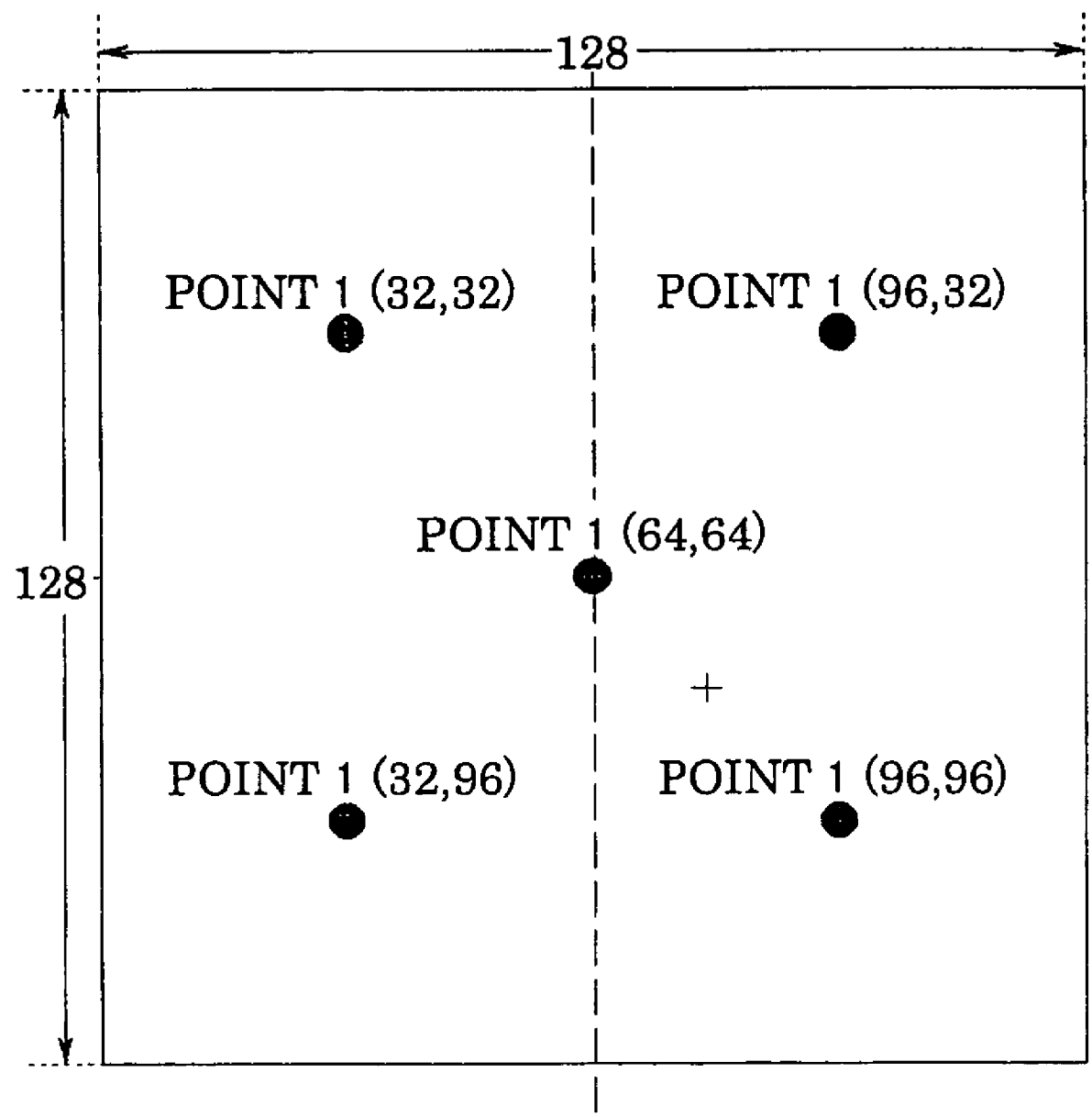
FIG. 8 is a plan view that shows a position of a pixel to which the correction is applied.
Figure 9A:
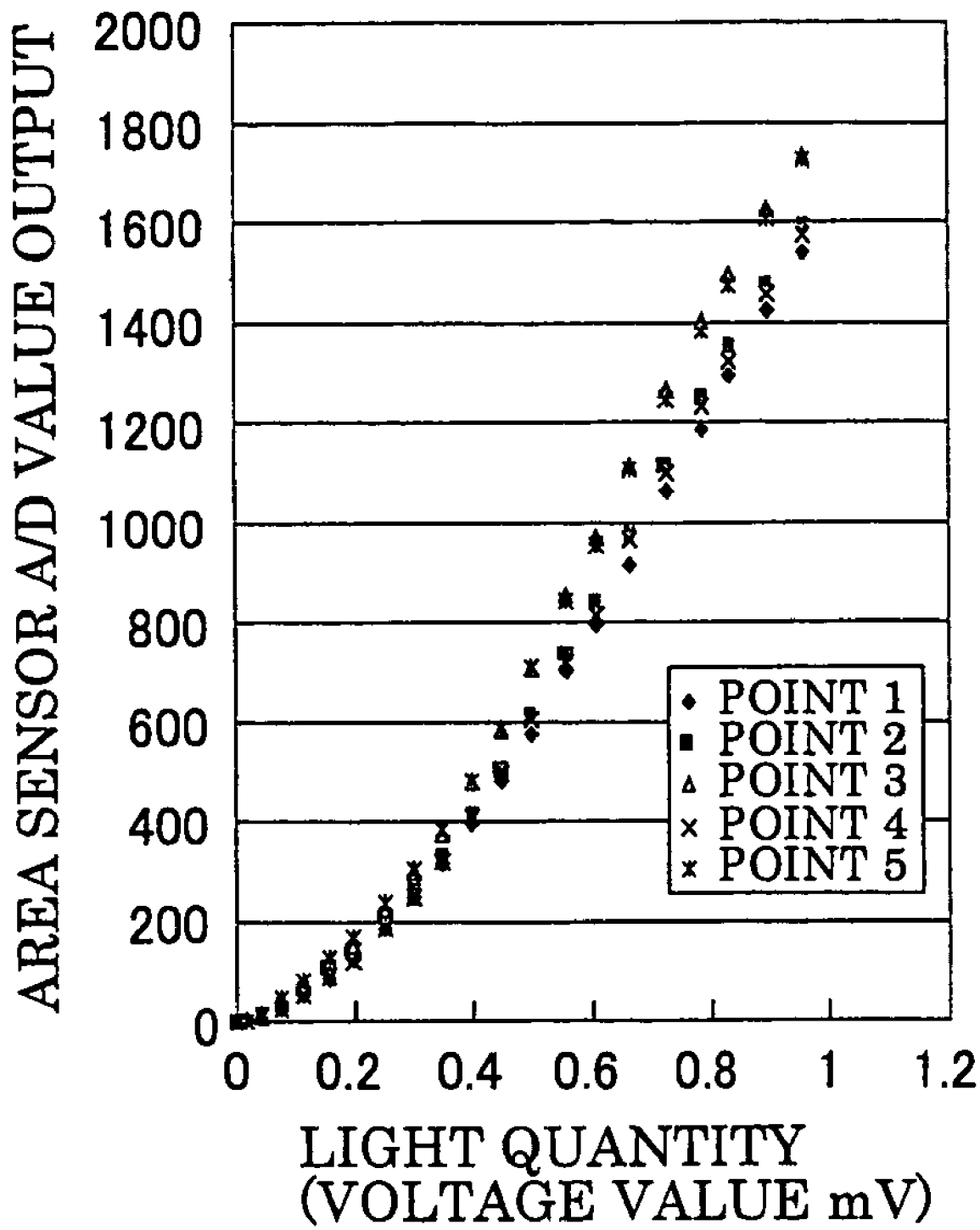
FIG. 9(a) is a graph that shows respective pixel outputs of an image sensor when a white plate is used as a test piece.

FIG. 9(a) shows a graph that indicates outputs at five points of the area sensor shown in FIG. 8 when the quantity of light of the LEDs 4 is varied with a white plate (ND: 9.5, actual value of reflection factor: 87.00%) being used as the test piece 2.

Figure 9B:
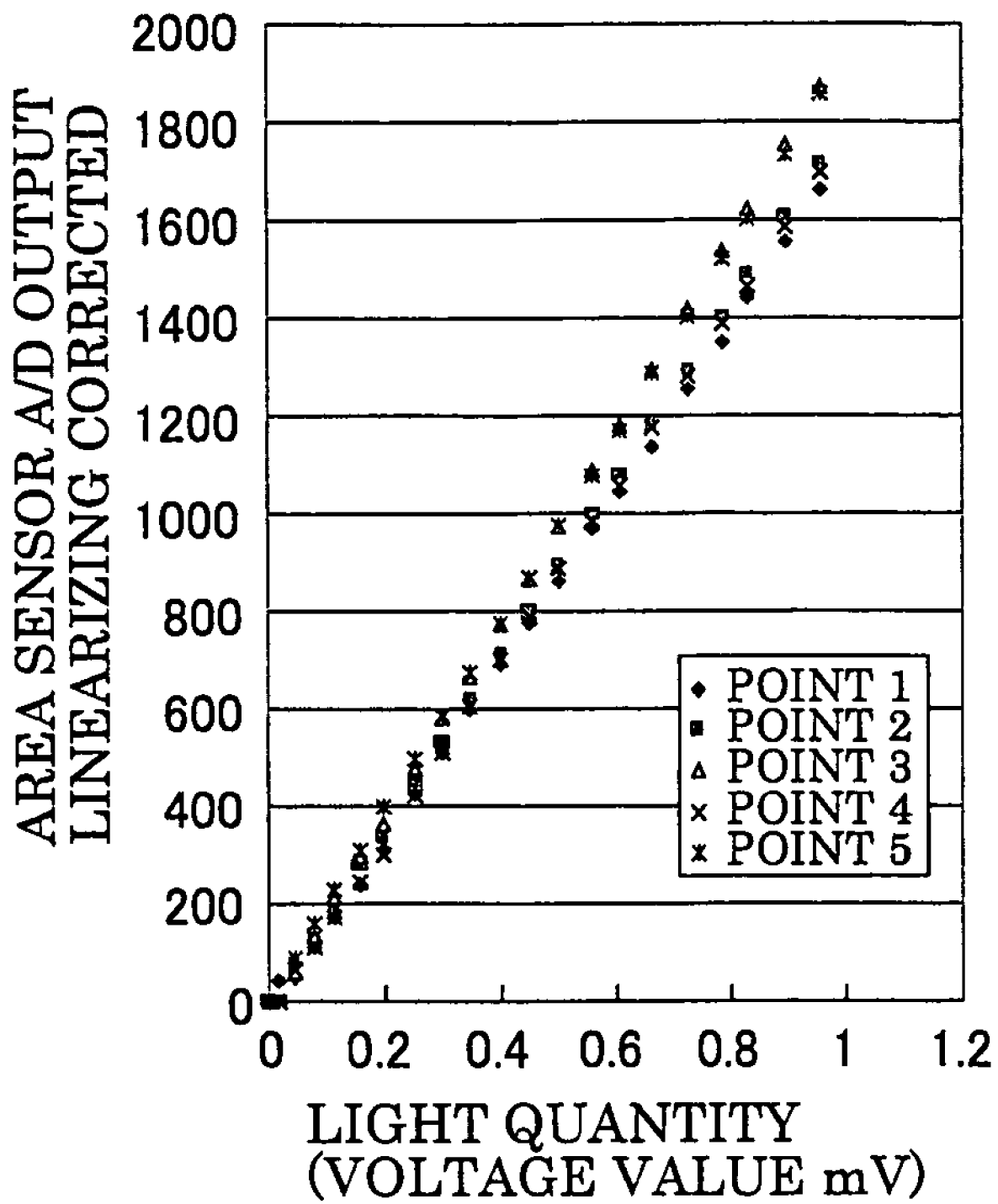
FIG. 9(b) is a graph that shows an output after a PD voltage-value conversion.

When the image sensor output (A/D count value) is converted (PD voltage-value conversion) to a voltage value of the photodetector based upon the relationship indicated by the graph of FIG. 5, the resulting correction as shown in FIG. 9(b) is obtained. In FIG. 9(b), there are differences among the quantities of reflected light at the respective points due to influences resulting from light irregularities and the like; however, the respective points are allowed to have a direct proportional relationship with respect to the quantity of light of the LEDs 4.

Figure 9C:
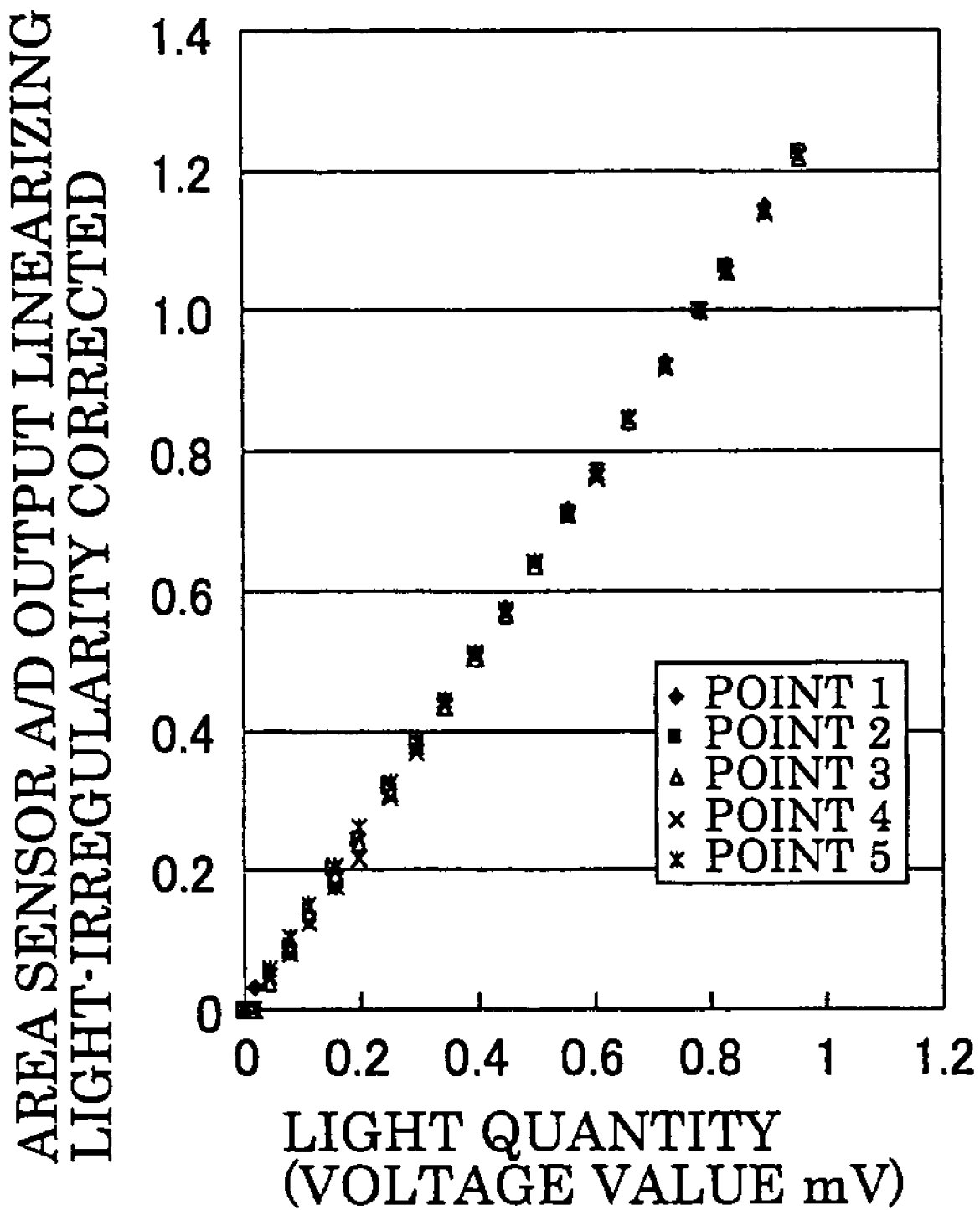
FIG. 9(c) is a graph obtained when the output of FIG. 9(b) is further subjected to a light irregularity correction process.

FIG. 9(c) shows a graph in which the light irregularities are corrected by applying the light-irregularity correction data to FIG. 9(b). The respective points are plotted along virtually the same line. The reason that, in FIG. 9(c), five points are completely made coincident with each other when the correction output of the image sensor is 1 is because light irregularities from the white plate data at this brightness have been corrected. FIG. 9(c) also shows that as the quantity of light decreases, the respective points come to deviate, resulting in degradation in correction precision.

(Example of Area Correction)

Figure 10A:
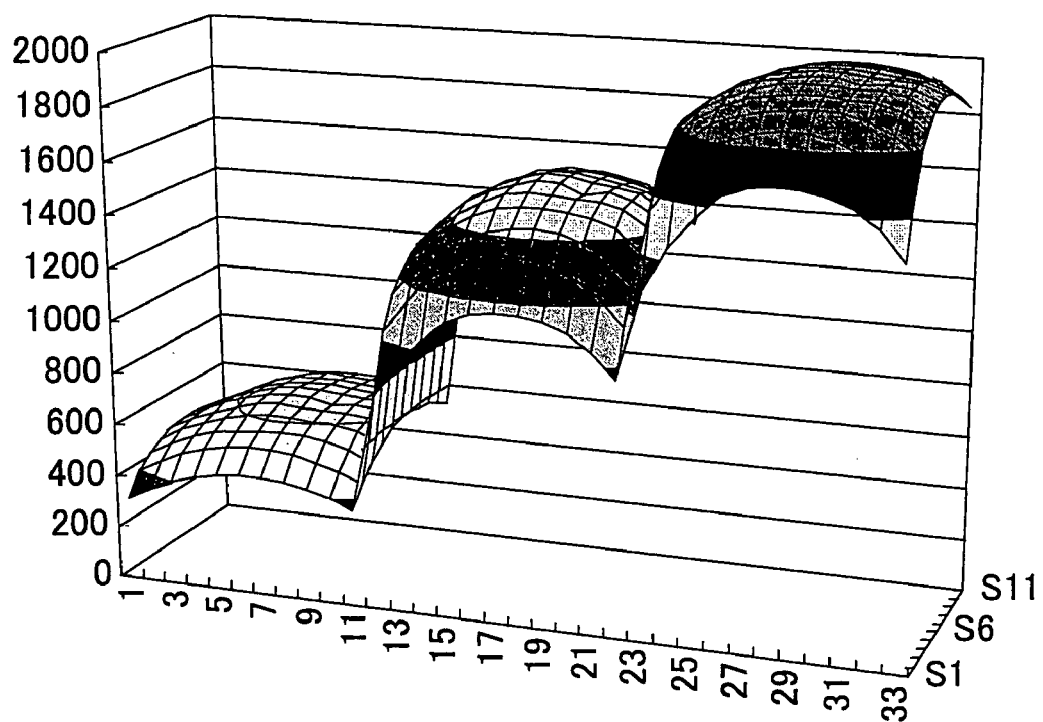
FIG. 10(a) is a drawing in which: images of a white plate are picked up in a divided manner in three stages from dark to bright in the quantity of LED light quantity to form three-dimensional contour face graphs.

FIG. 10(a) shows a graph that is obtained by picking up images of the white plate (ND: 9.5, actual value of reflection factor 87.00%) in a manner so as to be divided three stages from dark to bright in the quantity of LEDs light (all the image angle range is occupied by the white plate area), and aligning the pieces of image information to form a three-dimensional contour face graph. The contour face is formed by dividing the image into 10×10 areas and using the average value of pixels contained in each of the areas. With respect to the three dome-shaped white plate data, the data on the left end relates to the smallest quantity of light and the data on the right end relates to the greatest quantity of light.

The white plate data on the right end has a narrow difference between the maximum value and the minimum value even though the quantity of light thereof is greater than that of the white plate data in the middle. This is because the pixel quantity of light at a brighter portion of the white plate is close to the saturated quantity.

Figure 10B:
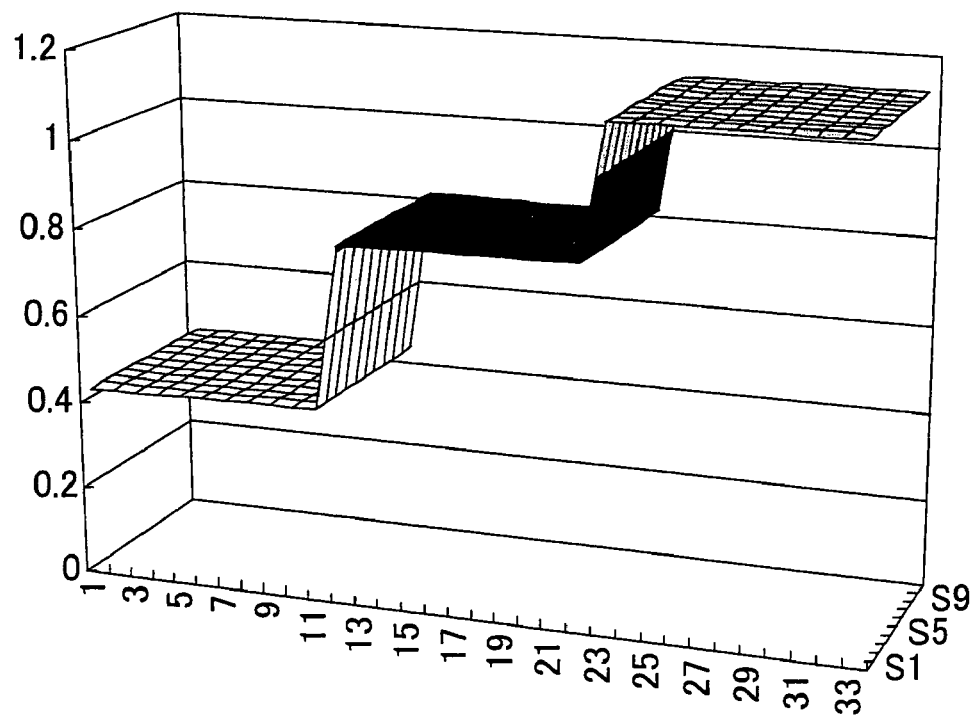
FIG. 10(b) shows a state in which a light-irregularity correction process is carried out on the graph of FIG. 10(a).

When the light-irregularity correction is carried out on the graph of FIG. 10(a), a flat graph is obtained as shown in FIG. 10(b).

(Simultaneous Reproducibility 1)

With respect to the same pixel, images of pieces of ND papers having different reflection factors were picked up, and the simultaneous reproducibility, obtained in the case when the ratio of the density values of these was calculated as a reflection factor, was examined.

The following description will discuss the sequence of the processes.

(1) The current value of the LEDs 4 is set to 0 mA, and a dark (offset) image is picked up.

(2) Plates formed by bonding pieces of paper of ND 9.5 (actual value of reflection factor: 87.00%) and ND 6.5 (actual value of reflection factor: 36.21%) onto base plates are prepared, and images of these are alternately picked up ten times.

Figure 11:
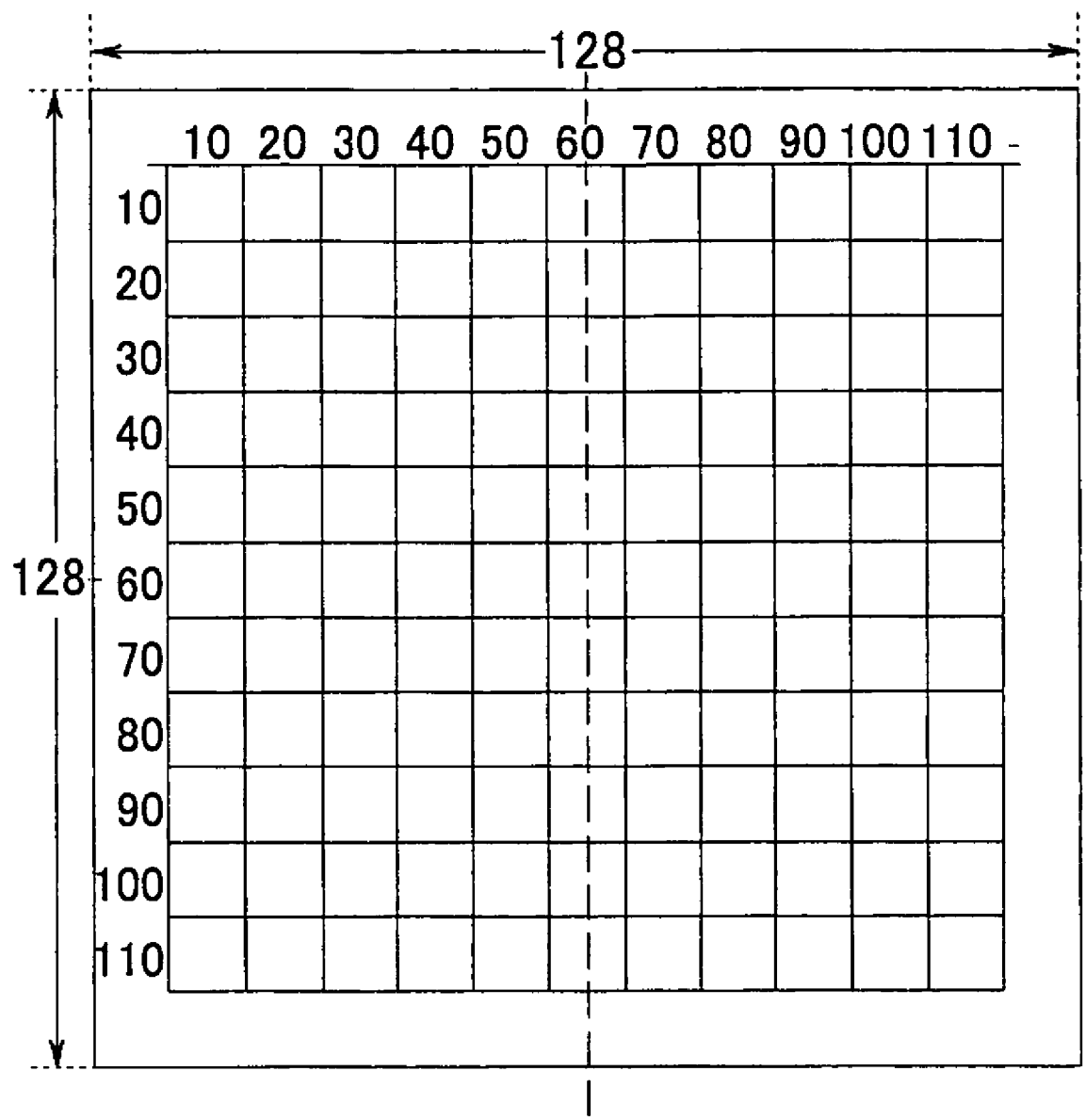
FIG. 11 is a plan view that shows an example in which one sheet of an image is divided into 11×11 areas.

(3) After light irregularities of the respective pixels have been corrected, one sheet of image is divided into 11×11 areas (each area containing 10×10=100 pixels) as shown in FIG. 11, and the average value of the quantities of light of the respective areas is calculated. The ratio of ND 9.5 and ND 6.5 of this average value of quantities of light is used as a reflection factor so that calculations are carried out on the respective areas.

Table 1 shows the results of measurements of one time among the measurements carried out ten times. The upper stage of this Table shows the average of light quantities of the respective areas obtained when an image of ND 9.5 is picked up, the intermediate stage thereof shows the average of light quantities of the respective areas obtained when an image of ND 6.5 is picked up, and the lower stage thereof shows the rate of respectively identical areas as the reflection factor.

TABLE 1

No. 1
LIGHT QUANTITY BLOCK AVERAGE DISTRIBUTION
(ND: 9.5, ACTUAL VALUE: 87.00%)

|     | 0 | 10 | 20 | 30 | 40 | 50 | 60 | 70 | 80 | 90 | 100 | 110 |
|-----|---|----|----|----|----|----|----|----|----|----|-----|-----|
| 0   |   |    |    |    |    |    |    |    |    |    |     |     |
| 10  |   | 1.023 | 1.023 | 1.024 | 1.022 | 1.022 | 1.022 | 1.022 | 1.022 | 1.022 | 1.022 | 1.022 |
| 20  |   | 1.024 | 1.023 | 1.023 | 1.023 | 1.023 | 1.023 | 1.023 | 1.023 | 1.023 | 1.022 | 1.021 |
| 30  |   | 1.023 | 1.023 | 1.023 | 1.023 | 1.024 | 1.023 | 1.023 | 1.023 | 1.023 | 1.023 | 1.023 |
| 40  |   | 1.022 | 1.024 | 1.023 | 1.023 | 1.023 | 1.023 | 1.023 | 1.023 | 1.023 | 1.023 | 1.023 |
| 50  |   | 1.023 | 1.024 | 1.023 | 1.024 | 1.023 | 1.022 | 1.023 | 1.023 | 1.022 | 1.024 | 1.023 |
| 60  |   | 1.023 | 1.023 | 1.023 | 1.023 | 1.022 | 1.022 | 1.023 | 1.023 | 1.023 | 1.023 | 1.022 |
| 70  |   | 1.023 | 1.023 | 1.023 | 1.023 | 1.023 | 1.023 | 1.022 | 1.022 | 1.023 | 1.022 | 1.022 |
| 80  |   | 1.023 | 1.024 | 1.024 | 1.024 | 1.023 | 1.022 | 1.023 | 1.023 | 1.022 | 1.022 | 1.022 |
| 90  |   | 1.023 | 1.024 | 1.024 | 1.023 | 1.023 | 1.022 | 1.023 | 1.023 | 1.023 | 1.022 | 1.023 |
| 100 |   | 1.023 | 1.024 | 1.024 | 1.023 | 1.023 | 1.023 | 1.023 | 1.022 | 1.023 | 1.023 | 1.022 |
| 110 |   | 1.025 | 1.023 | 1.023 | 1.024 | 1.023 | 1.023 | 1.023 | 1.023 | 1.023 | 1.023 | 1.022 |
| 120 |   |    |    |    |    |    |    |    |    |    |     |     |
|     | AVE. | 1.023 |  |  |  |  |  |  |  |  |  |  |
|     | C.V. (%) | 0.060 |  |  |  |  |  |  |  |  |  |  |
|     | ⊿ | 0.003 |  |  |  |  |  |  |  |  |  |  |

No. 1
LIGHT QUANTITY BLOCK AVERAGE DISTRIBUTION
(ND: 6.5, ACTUAL VALUE: 36.21%)

|     | 0 | 10 | 20 | 30 | 40 | 50 | 60 | 70 | 80 | 90 | 100 | 110 |
|-----|---|----|----|----|----|----|----|----|----|----|-----|-----|
| 0   |   |    |    |    |    |    |    |    |    |    |     |     |
| 10  |   | 0.419 | 0.419 | 0.423 | 0.421 | 0.420 | 0.421 | 0.422 | 0.426 | 0.431 | 0.438 | 0.450 |
| 20  |   | 0.421 | 0.420 | 0.422 | 0.423 | 0.422 | 0.422 | 0.423 | 0.426 | 0.431 | 0.439 | 0.445 |
| 30  |   | 0.419 | 0.421 | 0.422 | 0.424 | 0.423 | 0.422 | 0.422 | 0.425 | 0.429 | 0.437 | 0.444 |
| 40  |   | 0.419 | 0.423 | 0.423 | 0.421 | 0.420 | 0.421 | 0.422 | 0.424 | 0.426 | 0.433 | 0.442 |
| 50  |   | 0.419 | 0.421 | 0.422 | 0.421 | 0.419 | 0.420 | 0.420 | 0.422 | 0.425 | 0.432 | 0.439 |
| 60  |   | 0.418 | 0.421 | 0.421 | 0.420 | 0.419 | 0.419 | 0.420 | 0.422 | 0.424 | 0.430 | 0.437 |
| 70  |   | 0.418 | 0.420 | 0.421 | 0.420 | 0.419 | 0.417 | 0.419 | 0.422 | 0.426 | 0.429 | 0.436 |
| 80  |   | 0.418 | 0.422 | 0.422 | 0.420 | 0.419 | 0.419 | 0.417 | 0.421 | 0.424 | 0.427 | 0.435 |
| 90  |   | 0.418 | 0.422 | 0.423 | 0.422 | 0.418 | 0.419 | 0.418 | 0.420 | 0.424 | 0.430 | 0.437 |
| 100 |   | 0.418 | 0.419 | 0.423 | 0.423 | 0.420 | 0.417 | 0.418 | 0.419 | 0.426 | 0.431 | 0.438 |
| 110 |   | 0.418 | 0.419 | 0.421 | 0.422 | 0.420 | 0.420 | 0.421 | 0.421 | 0.425 | 0.434 | 0.442 |
| 120 |   |    |    |    |    |    |    |    |    |    |     |     |
|     | AVE. | 0.424 |  |  |  |  |  |  |  |  |  |  |
|     | C.V. (%) | 1.610 |  |  |  |  |  |  |  |  |  |  |
|     | ⊿ | 0.032 |  |  |  |  |  |  |  |  |  |  |

TABLE 1-continued

No. 1
IDENTICAL AREA REFLECTION FACTOR

| | 0 | 10 | 20 | 30 | 40 | 50 | 60 | 70 | 80 | 90 | 100 | 110 |
|---|---|---|---|---|---|---|---|---|---|---|---|---|
| 0 | | | | | | | | | | | | |
| 10 | | 40.92 | 40.91 | 41.34 | 41.13 | 41.11 | 41.14 | 41.29 | 41.73 | 42.12 | 42.86 | 43.99 |
| 20 | | 41.06 | 41.04 | 41.29 | 41.33 | 41.22 | 41.22 | 41.40 | 41.63 | 42.16 | 42.93 | 43.56 |
| 30 | | 40.98 | 41.18 | 41.25 | 41.41 | 41.32 | 41.28 | 41.28 | 41.54 | 41.95 | 42.72 | 43.44 |
| 40 | | 41.01 | 41.26 | 41.31 | 41.19 | 41.04 | 41.12 | 41.26 | 41.45 | 41.70 | 42.36 | 43.21 |
| 50 | | 40.96 | 41.15 | 41.25 | 41.14 | 40.94 | 41.04 | 41.03 | 41.28 | 41.54 | 42.17 | 42.92 |
| 60 | | 40.87 | 41.18 | 41.14 | 41.03 | 41.00 | 40.99 | 41.07 | 41.25 | 41.48 | 42.07 | 42.73 |
| 70 | | 40.83 | 41.04 | 41.14 | 41.08 | 41.00 | 40.82 | 40.97 | 41.29 | 41.63 | 41.95 | 42.63 |
| 80 | | 40.90 | 41.20 | 41.21 | 41.00 | 40.99 | 40.99 | 40.81 | 41.16 | 41.51 | 41.81 | 42.55 |
| 90 | | 40.88 | 41.18 | 41.29 | 41.23 | 40.85 | 40.97 | 40.87 | 41.05 | 41.51 | 42.08 | 42.68 |
| 100 | | 40.83 | 40.96 | 41.32 | 41.39 | 41.05 | 40.77 | 40.86 | 40.99 | 41.61 | 42.14 | 42.87 |
| 110 | | 40.76 | 40.98 | 41.15 | 41.27 | 41.04 | 41.02 | 41.13 | 41.13 | 41.57 | 42.40 | 43.25 |
| 120 | | | | | | | | | | | | |
| AVE. | | 41.46 | 41.11 | | | | | | | | | |
| C.V. (%) | | 1.63 | 0.44 | | | | | | | | | |
| Δ | | 3.23 | 0.74 | | | | | | | | | |

In the Table, AVE. represents the average value, and C. V. (%) represents a rate of change, that is, (standard deviation/average value). Here, Δ represents a difference between the maximum value and the minimum value within the area.

Table 2 shows the average value (upper stage) of reflection factors of the respective areas as the result of the measurements of ten times and the deviations (lower stage) in reflection factor of the respective areas.

TABLE 2

| | | 0 | 10 | 20 | 30 | 40 | 50 | 60 | 70 | 80 | 90 | 100 | 110 |
|---|---|---|---|---|---|---|---|---|---|---|---|---|---|
| REFLECTION FACTOR AVERAGE (N = 10) | | | | | | | | | | | | | |
| | 0 | | | | | | | | | | | | |
| | 10 | | 41.08 | 41.05 | 41.44 | 41.23 | 41.20 | 41.22 | 41.40 | 41.86 | 42.21 | 42.99 | 44.09 |
| | 20 | | 41.21 | 41.15 | 41.38 | 41.42 | 41.32 | 41.30 | 41.50 | 41.75 | 42.26 | 43.06 | 43.64 |
| | 30 | | 41.10 | 41.29 | 41.34 | 41.50 | 41.39 | 41.35 | 41.33 | 41.60 | 42.04 | 42.80 | 43.53 |
| | 40 | | 41.14 | 41.37 | 41.38 | 41.29 | 41.14 | 41.20 | 41.31 | 41.54 | 41.78 | 42.44 | 43.31 |
| | 50 | | 41.05 | 41.32 | 41.37 | 41.24 | 41.02 | 41.13 | 41.09 | 41.40 | 41.62 | 42.27 | 43.00 |
| | 60 | | 41.01 | 41.30 | 41.27 | 41.16 | 41.10 | 41.08 | 41.16 | 41.37 | 41.59 | 42.17 | 42.84 |
| | 70 | | 40.98 | 41.18 | 41.25 | 41.19 | 41.11 | 40.96 | 41.11 | 41.38 | 41.72 | 42.05 | 42.75 |
| | 80 | | 41.01 | 41.35 | 41.27 | 41.11 | 41.10 | 41.09 | 40.93 | 41.27 | 41.60 | 41.90 | 42.64 |
| | 90 | | 41.05 | 41.33 | 41.42 | 41.29 | 41.00 | 41.06 | 40.96 | 41.15 | 41.60 | 42.18 | 42.79 |
| | 100 | | 41.02 | 41.11 | 41.44 | 41.47 | 41.17 | 40.88 | 41.00 | 41.09 | 41.73 | 42.25 | 42.96 |
| | 110 | | 40.95 | 41.10 | 41.32 | 41.38 | 41.12 | 41.16 | 41.22 | 41.20 | 41.67 | 42.49 | 43.36 |
| | 120 | | | | | | | | | | | | | |
| ALL AREAS | | 41.57 | | | | | | | | | | | |
| REFLECTION FACTOR DEVIATION C. V. (%)(N = 10) | | | | | | | | | | | | | |
| | 0 | | | | | | | | | | | | |
| | 10 | | 0.758 | 0.687 | 0.629 | 0.567 | 0.540 | 0.613 | 0.557 | 0.551 | 0.580 | 0.615 | 0.625 |
| | 20 | | 0.689 | 0.582 | 0.536 | 0.540 | 0.498 | 0.480 | 0.467 | 0.535 | 0.493 | 0.512 | 0.580 |
| | 30 | | 0.608 | 0.588 | 0.510 | 0.469 | 0.409 | 0.400 | 0.386 | 0.376 | 0.416 | 0.417 | 0.486 |
| | 40 | | 0.572 | 0.538 | 0.450 | 0.414 | 0.404 | 0.429 | 0.372 | 0.385 | 0.427 | 0.421 | 0.377 |
| | 50 | | 0.566 | 0.524 | 0.429 | 0.386 | 0.402 | 0.404 | 0.394 | 0.455 | 0.422 | 0.417 | 0.420 |
| | 60 | | 0.567 | 0.467 | 0.404 | 0.412 | 0.398 | 0.424 | 0.427 | 0.412 | 0.408 | 0.407 | 0.411 |
| | 70 | | 0.530 | 0.542 | 0.396 | 0.426 | 0.417 | 0.424 | 0.427 | 0.388 | 0.433 | 0.411 | 0.423 |
| | 80 | | 0.568 | 0.539 | 0.431 | 0.431 | 0.406 | 0.397 | 0.462 | 0.401 | 0.418 | 0.426 | 0.431 |

TABLE 2-continued

|     | 0 | 10 | 20 | 30 | 40 | 50 | 60 | 70 | 80 | 90 | 100 | 110 |
|-----|---|-----|-----|-----|-----|-----|-----|-----|-----|-----|-----|-----|
| 90  |   | 0.516 | 0.567 | 0.438 | 0.427 | 0.430 | 0.433 | 0.433 | 0.420 | 0.419 | 0.405 | 0.427 |
| 100 |   | 0.581 | 0.536 | 0.465 | 0.382 | 0.384 | 0.421 | 0.437 | 0.443 | 0.442 | 0.414 | 0.403 |
| 110 |   | 0.650 | 0.588 | 0.571 | 0.459 | 0.392 | 0.401 | 0.414 | 0.422 | 0.422 | 0.440 | 0.442 |

In comparison with reflection factors in the respective areas from Table 1 and Table 2, the deviation is smallest in the vicinity of the light axis of the lens 8 (or a portion in which irradiation light rays of the LEDs 4 are converged most closely), and the deviation tends to become greater as the distance from this point becomes greater in the form of a concentric circle. It is considered that this tendency occurs because the amount of correction becomes greater as the distance from the light axis becomes longer.

Moreover, in the case when the reflection factor is measured by using the image sensor, there is a considerable difference between reflection factors obtained separately in the respective areas, even when a test piece that is supposed to have even density is measured. The reason for this is because the light-irregularity correction precision differs depending on positions, and because density irregularities originally contained in the test piece give adverse effects.

(Simultaneous Reproducibility 2)

Pieces of ND papers having different reflection factors were placed within the same image, and the simultaneous reproducibility, obtained in the case when the ratio of the density values of these is calculated as a reflection factor, was examined. The following description will discuss the sequence of the processes.

(1) The current value of the LEDs 4 is set to 0 mV mA, and a dark (offset) image is picked up.

(2) A plate, formed by bonding pieces of papers of ND 9.5 (actual value of reflection factor 87.00%) and ND 6.5 (actual value of reflection factor 36.21%) onto a base plate with each of these entering half of the image angle, is prepared, and an image thereof is picked up ten times.

Figure 12:
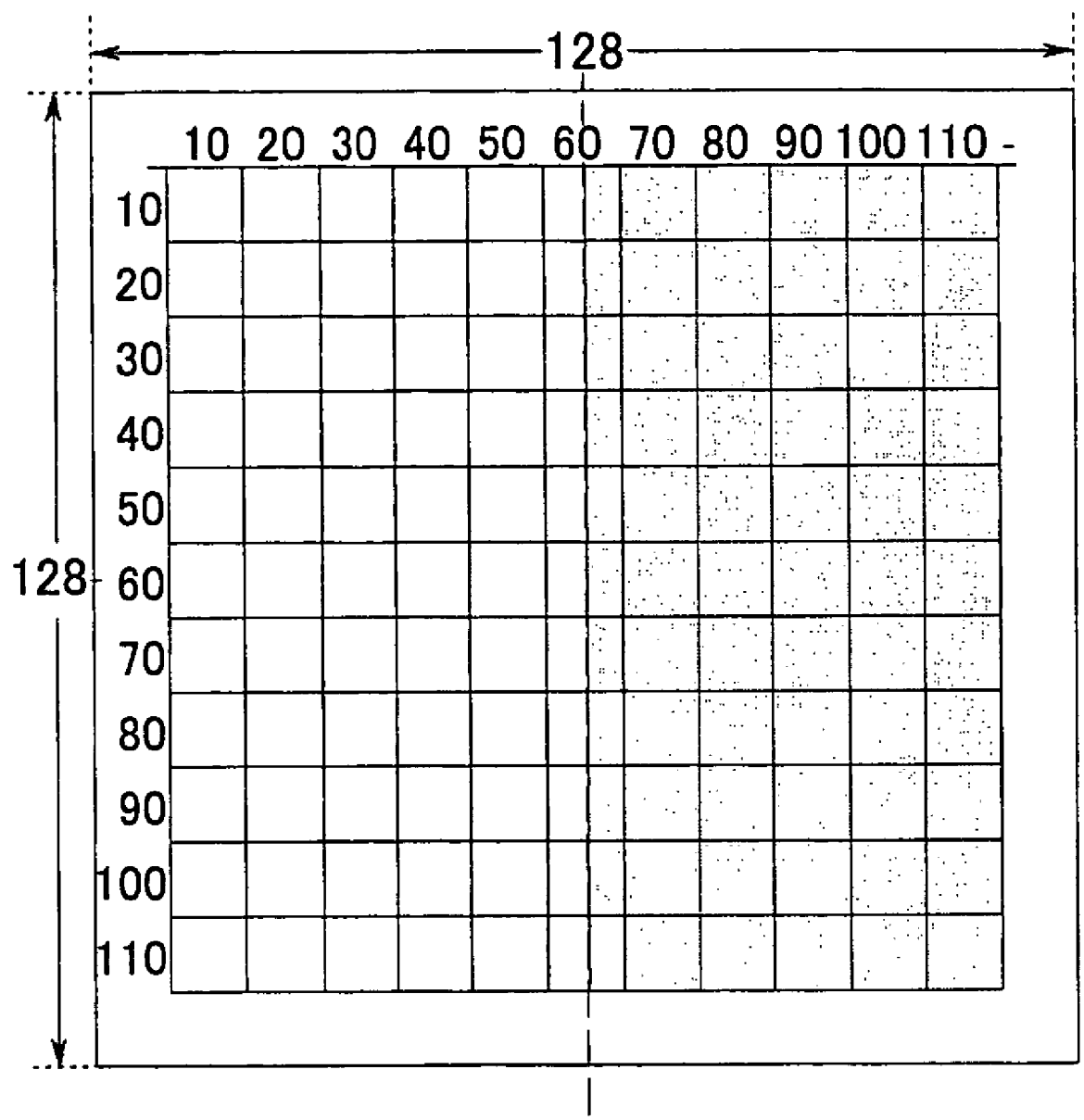
FIG. 12 is a plan view that shows another example in which one sheet of an image is divided into 11×11 areas.

(3) After light irregularities of the respective pixels have been corrected, one sheet of image is divided into 11×11 areas (each area containing 10×10=100 pixels) as shown in FIG. 12, and the average value of the quantities of light of the respective areas is calculated. The ratio of ND 9.5 and ND 6.5 of this average value of quantities of light is used as a reflection factor so that the reflection factors of the respective areas are calculated.

Table 3 shows the results of measurements of one time among the measurements carried out ten times. The left side on the upper stage of Table 3 shows the average of light quantities of the respective areas relating to ND 9.5, and the right side on the upper stage thereof shows the average of light quantities of the respective areas relating to ND 6.5. The left side on the lower stage shows a case in which, supposing that a portion at which ND 9.5 and ND 6.5 intersect with each other within the image is a center line, a ratio that is obtained based upon this line in a line-symmetrical manner is used as a reflection factor (referred to as symmetrical reflection factor). Moreover, the right side on the lower stage shows a case in which the area is divided into areas of ND 9.5 and ND 6.5 by the center line, with the ratio of the respectively identical areas (for example: area of lateral axis 10 and area of lateral axis 50, area of lateral axis 50 and area of lateral axis 10) being used as a reflection factor (referred to as one-directional reflection factor).

TABLE 3

No. 1
LIGHT QUANTITY BLOCK AVERAGE DISTRIBUTION

|     | 10 | 20 | 30 | 40 | 50 | 60 | 70 | 80 | 90 | 100 | 110 |
|-----|-----|-----|-----|-----|-----|-----|-----|-----|-----|-----|-----|
| 10  | 0.997 | 0.999 | 1.001 | 0.996 | 0.990 |   | 0.458 | 0.458 | 0.460 | 0.467 | 0.474 |
| 20  | 0.995 | 0.994 | 0.994 | 0.995 | 0.989 |   | 0.455 | 0.455 | 0.458 | 0.463 | 0.468 |
| 30  | 0.992 | 0.990 | 0.991 | 0.993 | 0.990 |   | 0.453 | 0.451 | 0.452 | 0.459 | 0.464 |
| 40  | 0.994 | 0.991 | 0.991 | 0.992 | 0.989 |   | 0.452 | 0.450 | 0.450 | 0.455 | 0.461 |
| 50  | 0.990 | 0.990 | 0.993 | 0.992 | 0.988 |   | 0.449 | 0.449 | 0.448 | 0.453 | 0.458 |
| 60  | 0.992 | 0.991 | 0.993 | 0.990 | 0.989 |   | 0.449 | 0.447 | 0.448 | 0.451 | 0.455 |
| 70  | 0.991 | 0.989 | 0.995 | 0.994 | 0.991 |   | 0.447 | 0.447 | 0.448 | 0.450 | 0.453 |
| 80  | 0.990 | 0.992 | 0.996 | 0.994 | 0.990 |   | 0.448 | 0.447 | 0.447 | 0.450 | 0.455 |
| 90  | 0.992 | 0.991 | 0.998 | 0.997 | 0.992 |   | 0.448 | 0.446 | 0.447 | 0.451 | 0.454 |
| 100 | 0.994 | 0.992 | 1.001 | 1.001 | 0.997 |   | 0.448 | 0.445 | 0.448 | 0.451 | 0.456 |
| 110 | 0.995 | 0.993 | 0.997 | 1.001 | 0.996 |   | 0.448 | 0.445 | 0.448 | 0.452 | 0.460 |

| C.V. (%) | 0.33 |
| Δ | 0.013 |

| C.V. (%) | 1.40 |
| Δ | 0.030 |

TABLE 3-continued

| | No. 1 SYMMETRICAL REFLECTION FACTOR | | | | | ONE-DIRECTIONAL REFLECTION FACTOR | | | | |
|---|---|---|---|---|---|---|---|---|---|---|
| | 10/110 | 20/100 | 30/90 | 40/80 | 50/70 | 10/70 | 20/80 | 30/90 | 40/100 | 50/110 |
| 10 | 47.58 | 46.78 | 45.98 | 46.01 | 46.31 | 45.96 | 45.89 | 45.98 | 46.90 | 47.94 |
| 20 | 47.02 | 46.64 | 46.12 | 45.73 | 45.98 | 45.71 | 45.81 | 46.12 | 46.56 | 47.29 |
| 30 | 46.73 | 46.36 | 45.64 | 45.35 | 45.73 | 45.64 | 45.49 | 45.64 | 46.22 | 46.83 |
| 40 | 46.38 | 45.87 | 45.40 | 45.40 | 45.69 | 45.47 | 45.45 | 45.40 | 45.83 | 46.60 |
| 50 | 46.21 | 45.73 | 45.10 | 45.28 | 45.46 | 45.36 | 45.39 | 45.10 | 45.61 | 46.30 |
| 60 | 45.91 | 45.47 | 45.06 | 45.12 | 45.41 | 45.28 | 45.07 | 45.06 | 45.52 | 46.04 |
| 70 | 45.77 | 45.54 | 45.08 | 45.00 | 45.12 | 45.13 | 45.23 | 45.08 | 45.31 | 45.77 |
| 80 | 45.94 | 45.38 | 44.92 | 44.96 | 45.19 | 45.21 | 45.06 | 44.92 | 45.28 | 45.92 |
| 90 | 45.81 | 45.46 | 44.82 | 44.74 | 45.12 | 45.13 | 44.98 | 44.82 | 45.21 | 45.80 |
| 100 | 45.86 | 45.44 | 44.77 | 44.44 | 44.93 | 45.06 | 44.83 | 44.77 | 45.05 | 45.73 |
| 110 | 46.20 | 45.54 | 44.87 | 44.42 | 45.00 | 45.02 | 44.79 | 44.87 | 45.16 | 46.18 |
| AVE. | 45.60 | 45.29 | | | | AVE. | 45.60 | 45.29 | | |
| C.V. (%) | 1.42 | 0.63 | | | | C.V. (%) | 1.45 | 0.55 | | |
| Δ | 3.17 | 0.95 | | | | Δ | 3.17 | 0.91 | | |

Table 4 shows the average value (upper stage) and deviation (lower stage) obtained by carrying out calculations as shown on the lower stage of Table 3 corresponding to measurements of ten times.

TABLE 4

| | SYMMETRICAL REFLECTION FACTOR AVERAGE (N = 10) | | | | | ONE-DIRECTIONAL REFLECTION FACTOR AVERAGE (N = 10) | | | | |
|---|---|---|---|---|---|---|---|---|---|---|
| | 10/110 | 20/100 | 30/90 | 40/80 | 50/70 | 10/70 | 20/80 | 30/90 | 40/100 | 50/110 |
| 10 | 47.54 | 46.77 | 46.05 | 46.02 | 46.32 | 45.95 | 45.91 | 46.05 | 46.88 | 47.92 |
| 20 | 47.05 | 46.67 | 46.10 | 45.73 | 46.01 | 45.74 | 45.82 | 46.10 | 46.59 | 47.34 |
| 30 | 46.78 | 46.33 | 45.66 | 45.36 | 45.71 | 45.63 | 45.51 | 45.66 | 46.18 | 46.86 |
| 40 | 46.37 | 45.88 | 45.44 | 45.44 | 45.68 | 45.47 | 45.49 | 45.44 | 45.83 | 46.59 |
| 50 | 46.24 | 45.72 | 45.11 | 45.29 | 45.43 | 45.34 | 45.40 | 45.11 | 45.61 | 46.33 |
| 60 | 45.90 | 45.48 | 45.07 | 45.15 | 45.42 | 45.28 | 45.11 | 45.07 | 45.52 | 46.05 |
| 70 | 45.82 | 45.57 | 45.08 | 45.04 | 45.13 | 45.14 | 45.26 | 45.08 | 45.35 | 45.81 |
| 80 | 45.93 | 45.40 | 44.95 | 44.98 | 45.20 | 45.21 | 45.07 | 44.95 | 45.31 | 45.92 |
| 90 | 45.85 | 45.46 | 44.82 | 44.73 | 45.15 | 45.15 | 44.97 | 44.82 | 45.22 | 45.85 |
| 100 | 45.88 | 45.45 | 44.75 | 44.44 | 44.93 | 45.06 | 44.83 | 44.75 | 45.05 | 45.75 |
| 110 | 46.19 | 45.58 | 44.84 | 44.42 | 44.98 | 45.01 | 44.82 | 44.84 | 45.18 | 46.16 |
| ALL AREAS | 45.61 | C.V. (%) | 1.42 | 0.63 | | ALL AREAS | 45.61 | C.V. (%) | 1.45 | 0.54 |
| | | Δ | 3.12 | 0.94 | | | | Δ | 3.17 | 0.89 |

TABLE 4-continued

| | SYMMETRICAL REFLECTION FACTOR C. V (%) (N = 10) | | | | | ONE-DIRECTIONAL REFLECTION FACTOR C. V (%) (N = 10) | | | | |
|---|---|---|---|---|---|---|---|---|---|---|
| | 10/110 | 20/100 | 30/90 | 40/80 | 50/70 | 10/70 | 20/80 | 30/90 | 40/100 | 50/110 |
| 10 | 0.37 | 0.36 | 0.34 | 0.34 | 0.35 | 0.31 | 0.33 | 0.34 | 0.37 | 0.41 |
| 20 | 0.34 | 0.29 | 0.25 | 0.25 | 0.26 | 0.24 | 0.24 | 0.25 | 0.31 | 0.36 |
| 30 | 0.24 | 0.23 | 0.21 | 0.24 | 0.22 | 0.20 | 0.25 | 0.21 | 0.22 | 0.26 |
| 40 | 0.23 | 0.26 | 0.23 | 0.20 | 0.20 | 0.21 | 0.20 | 0.23 | 0.25 | 0.22 |
| 50 | 0.22 | 0.22 | 0.22 | 0.22 | 0.20 | 0.19 | 0.22 | 0.22 | 0.22 | 0.22 |
| 60 | 0.22 | 0.19 | 0.19 | 0.21 | 0.19 | 0.18 | 0.21 | 0.19 | 0.19 | 0.22 |
| 70 | 0.23 | 0.17 | 0.21 | 0.21 | 0.19 | 0.22 | 0.20 | 0.21 | 0.18 | 0.21 |
| 80 | 0.20 | 0.22 | 0.18 | 0.22 | 0.20 | 0.19 | 0.22 | 0.18 | 0.22 | 0.21 |
| 90 | 0.24 | 0.21 | 0.23 | 0.22 | 0.20 | 0.20 | 0.23 | 0.23 | 0.21 | 0.24 |
| 100 | 0.23 | 0.24 | 0.22 | 0.23 | 0.20 | 0.19 | 0.23 | 0.22 | 0.24 | 0.25 |
| 110 | 0.24 | 0.25 | 0.23 | 0.21 | 0.21 | 0.18 | 0.21 | 0.23 | 0.24 | 0.26 |
| ALL AREAS | 0.23 | | | | | ALL AREAS | 0.23 | | | |

In comparison with the results of simultaneous reproducibility 1, the results of simultaneous reproducibility 2 provide values that are approximately two times superior in C. V. (%). The reason for this is because, in the measurements of simultaneous reproducibility 1, the measuring subjects need to be exchanged with the hands for each of the measurements, while, in the measurements of simultaneous reproducibility 2, it is not necessary to touch the measuring subjects with the hands. In other words, the results of simultaneous reproducibility 2 are considered to be close to the inherent image-pickup reproducibility of the CMOS image sensor.

(Reflection Factor Linearity)

A known spectrophotometer (MINOLTA CM-503c: using no area sensor) whose precision had been controlled was used to measure plurality of kinds of ND papers having different reflection factors so that the correlation with the reflection-factor measuring device of the embodiment of the present invention was examined.

The reflection factors of a plurality of kinds of ND papers to be used were preliminarily measured by using the spectrophotometer. The reflection factors were measured at randomly selected five points on the ND papers, and the average values were used.

(1) The current value of the LEDs 4 is set to 0 mA, and a dark (offset) image is picked up.

(2) An image of the ND paper that has been preliminarily measured by the spectrophotometer is picked up.

(3) As shown in FIG. 8, light-irregularity correction processes are carried out on five points (pixels) that are evenly distributed on each image.

Figure 13:
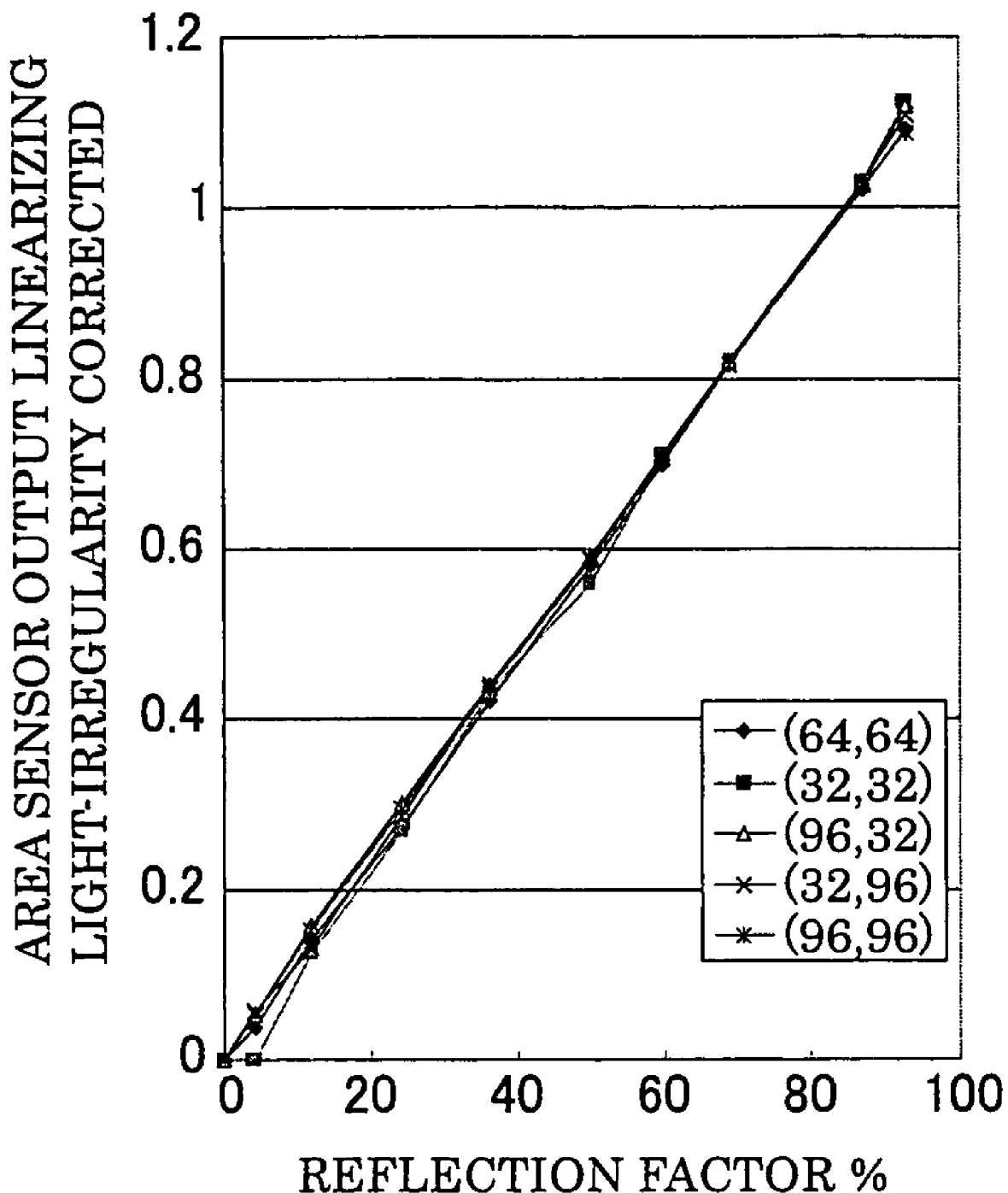
FIG. 13 is a drawing that shows a state in which 5 points of each image shown in FIG. 8 have been subjected to light-irregularity corrections, and plotted.

FIG. 13 shows a graph in which values measured by the spectrophotometer are plotted on the axis of abscissas, while the five points (pixels) of each image shown in FIG. 8 are light-irregularity-corrected by the present invention and the resulting values are plotted on the axis of ordinates.

The results shown in the graph of FIG. 13 are obtained not on an area average basis, but on a pixel unit basis; however, pixel point 3 (96, 32) or the like close to the light axis has good linearity. Point 1 (32, 32) is a pixel that exhibits the darkest value among the five pixels (with respect to raw data), with the poorest linearity among the five pixels. These experiments also show that it is difficult to carry out the light-irregularity correction on portions separated from the light axis.

(Temperature Characteristics)

Measurements were carried out so as to confirm the temperature characteristics of the reflection-factor measuring device of the present embodiment.

The following operations were carried out after the system (with the power switch being turned on) had sufficiently adapted to respective environments at 10° C., 20° C. and 30° C. A member, formed by bonding ND 9.5 (reflection factor actual measured value 87.00%) and ND 6.5 (reflection factor actual measured value 36.21%) to a base plate with each of these entering half of the image angle, was used as a test piece.

(1) The current value of the LEDs 4 is set to 0 mA, and a dark (offset) image is picked up.

(2) The current value of the LEDs 4 is set to (10° C.:16.52 (mA), 20° C.:17.20 (mA), 30° C.:17.95 (mA)) at the respective environment temperatures, and the sequence enters a stand-by state waiting for the LEDs light quantity to be detected by the photodetector to exceed the respective temperatures (10° C.:0.788 (V), 20° C.:0.786 (V), 30° C.:0.783 (V)).

(3) Immediately after the conditions of (2) have been satisfied, images are picked up. The above-mentioned operations are repeated ten times.

Table 5 shows the results of all-area average reflection factor at each of the temperatures obtained by the respective measurements of ten times. Here, S.D. represents the standard deviation.

TABLE 5

| | AVERAGE REFLECTION FACTOR (%) TEMPERATURE CHARACTERISTICS | | |
|---|---|---|---|
| | ENVIRONMENT TEMPERATURE | | |
| | 10° C. | 20° C. | 30° C. |
| No. 1 | 45.09 | 45.24 | 45.64 |
| No. 2 | 44.94 | 45.31 | 45.77 |

TABLE 5-continued

AVERAGE REFLECTION FACTOR (%)
TEMPERATURE CHARACTERISTICS

| | ENVIRONMENT TEMPERATURE | | |
|---|---|---|---|
| | 10° C. | 20° C. | 30° C. |
| No. 3 | 45.44 | 45.10 | 45.61 |
| No. 4 | 45.16 | 45.30 | 45.58 |
| No. 5 | 45.02 | 45.21 | 45.38 |
| No. 6 | 44.81 | 45.08 | 45.72 |
| No. 7 | 45.01 | 45.39 | 45.50 |
| No. 8 | 45.15 | 45.16 | 45.73 |
| No. 9 | 45.06 | 45.45 | 45.53 |
| No. 10 | 44.82 | 45.41 | 45.59 |
| AVE. | 45.05 | 45.26 | 45.60 |
| S.D. | 0.184 | 0.129 | 0.118 |
| C.V.(%) | 0.41 | 0.29 | 0.26 |
| $\Delta$ | 0.63 | 0.37 | 0.39 |

The results show that there are hardly any influences caused by environment temperatures, and the temperature tendency is approximately 0.28 (%/10° C.)

(Drift Characteristics)

Measurements were carried out so as to confirm the drift tendency of the reflection-actor measuring device of the present embodiment in the applied state (including time and temperature).

(1) Thermocouples are attached to main units (the inside of the driving circuit 20, the vicinity of the LEDs 4, the vicinity of the area sensor 8) of the reflection-factor measuring device of the embodiment so as to monitor the temperature.

(2) The reflection-factor measuring device is allowed to sufficiently adapt to the environment with the power-supply being turned off.

(3) The current value of the LEDs 4 is set to 0 mA, and a dark (offset) image is picked up.

(4) The current value of the LEDs 4 is set to 17.3 (mA), and the sequence enters a stand-by state waiting for the LEDs light quantity to be detected by the photodetector 10 to exceed 0.789 (V).

(5) Immediately after the above-mentioned condition has been satisfied, image-pickup operations are carried out three times.

(6) The processes of (3) to (5) are repeated every 10 minutes, until all the monitoring unit temperatures have entered an equilibrium state.

Figure 14:
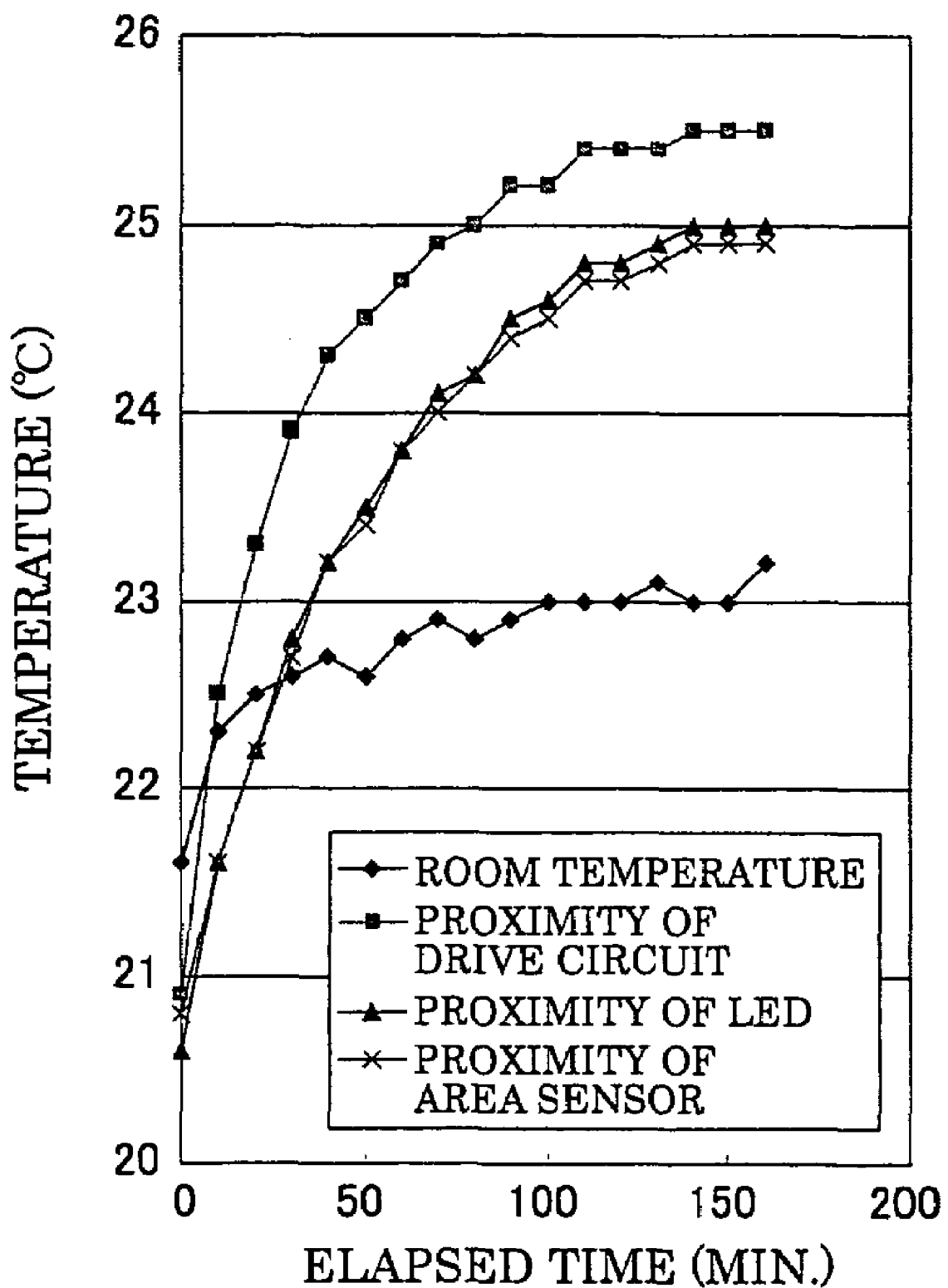
FIG. 14 is a drawing that shows the relationship between the elapsed time and temperature in main units of a reflection-factor measuring device of an embodiment of FIG. 14.

The graph of FIG. 14 shows the relationship between the elapsed time (every 10 minutes) and the temperature in the main units (the vicinity of the drive circuit 20, the vicinity of the LEDs 4, the vicinity of the area sensor 8) of the reflection-factor measuring device of the embodiment.

Figure 15:
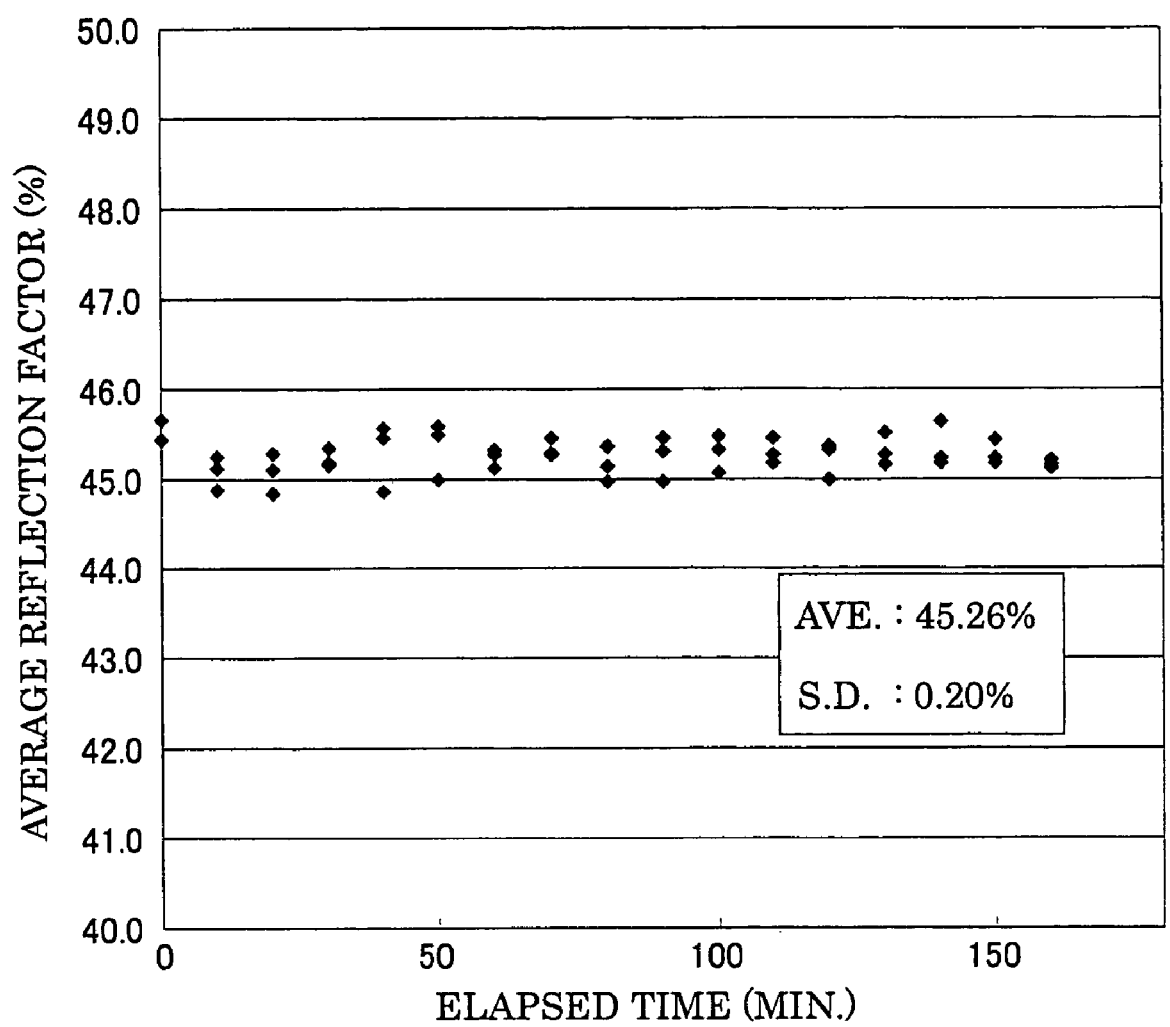
FIG. 15 is a drawing in which the results of measurements carried out on the reflection factor three times every 10 minutes.

FIG. 15 shows a graph in which the resulting reflection factors, obtained by carrying out measurements three times every 10 minutes, are plotted.

From the results of FIG. 14 and FIG. 15, no drift phenomenon is confirmed in the applied state (including temperature and time), and even if there is some, the degree thereof is so small that it is included in deviations occurring in each simultaneous measuring process.

As a result of the above-mentioned examination, in the reflection-factor measuring device of the present embodiment, it is confirmed that there is hardly any drift tendency in the applied state (including time and temperature) in which C. V.=0.23% (in the vicinity of a reflection factor of 45%) with respect to the simultaneous reproducibility (n=10) and 0.28 (%/10° C.) in the vicinity of a reflection factor of 45% with respect to the temperature characteristics.

It is found that the CMOS image sensor used in the present embodiment may be sufficiently applied to measurements in a semi-determination level of a measuring device for urine test paper and the like.

EMBODIMENT 2

Figure 16:
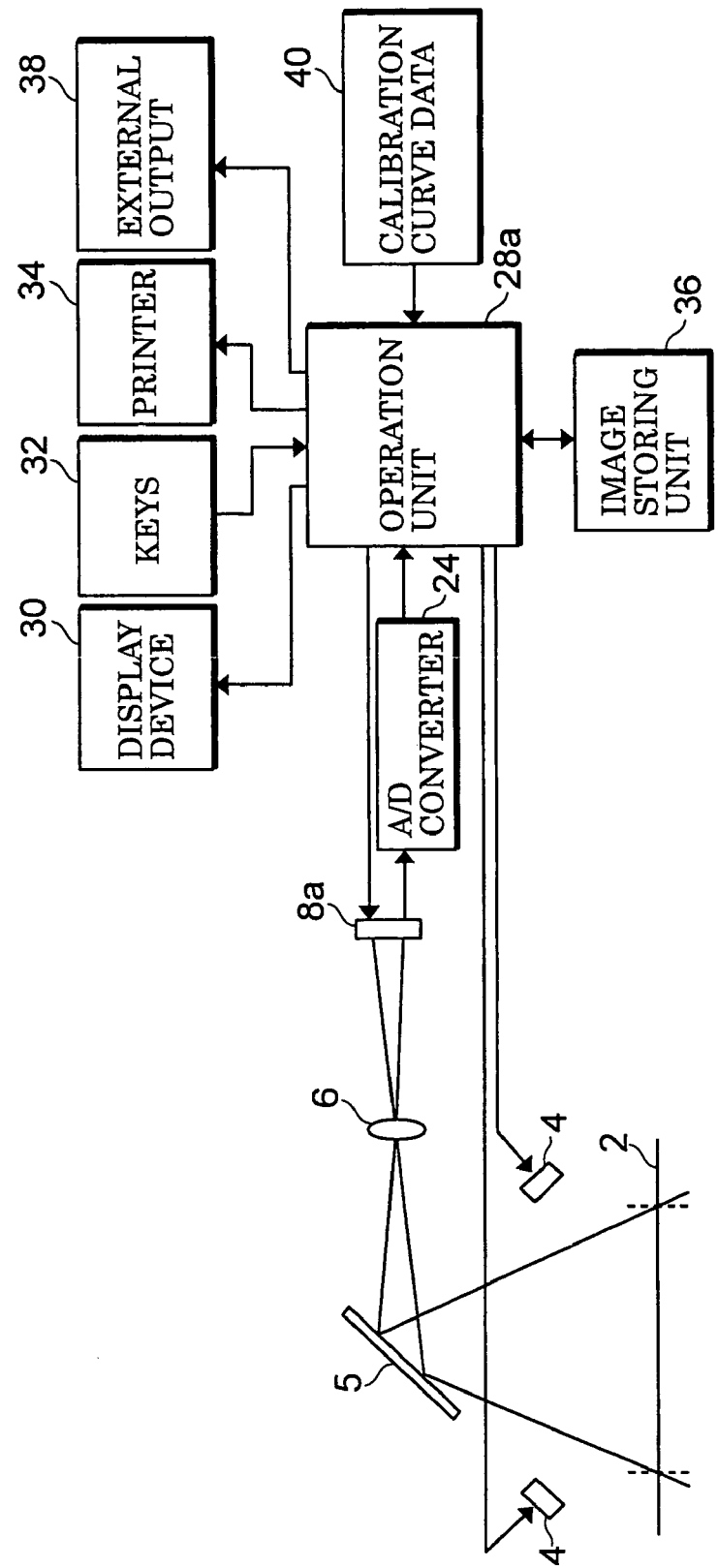
FIG. 16 is a structural drawing that shows a second embodiment of a reflection-factor measuring device of the present invention as a partial block diagram.

With respect to a second embodiment of a reflection-factor measuring device, FIG. 16 shows one example to which an output correction method in accordance with the second aspect of the present invention is applied.

In comparison with the reflection-factor measuring device of FIG. 3, the present device is different in that a photodetector 10 for monitoring the quantity of light is not installed. The other structure is basically the same. Reflected light of a test piece 2 is converged on an area sensor 8a as an image by a lens 6 through a reflection plate 5. The area sensor 8a includes devices up to the amplifier 22 shown in FIG. 3. The detection signal of the area sensor 8a is taken into a calculation unit 28a through an A/D converter 24. This calculation unit 28a corresponds to the RAM 26 and the personal computer 28 in FIG. 3. A display device 30, a keyboard 32 and a printer 34 are connected to the calculation unit 28a. Reference numeral 36 represents an image storing unit for storing acquired image data, which is constituted by, for example, a hard disk device. Calibration curve data 40, which is used for converting the reflection factor calculated by the calculation unit 28a to density, is stored in the hard disk device or a floppy disk device.

The results of the data processing in the calculation unit 28a are taken out to a necessary external device as an external output 38.

In this embodiment, in order to acquire the relationship between the output of the area sensor 8a and the reflection factor of the test piece 2 as linearizing data, a reference plate having a known reflection factor is measured as the test piece 2. With respect to the standard plates, pieces of ND papers are used, and those of 11 stages are prepared ranging one plate having the greatest reflection factor to another plate having the smallest reflection factor.

Figure 17:
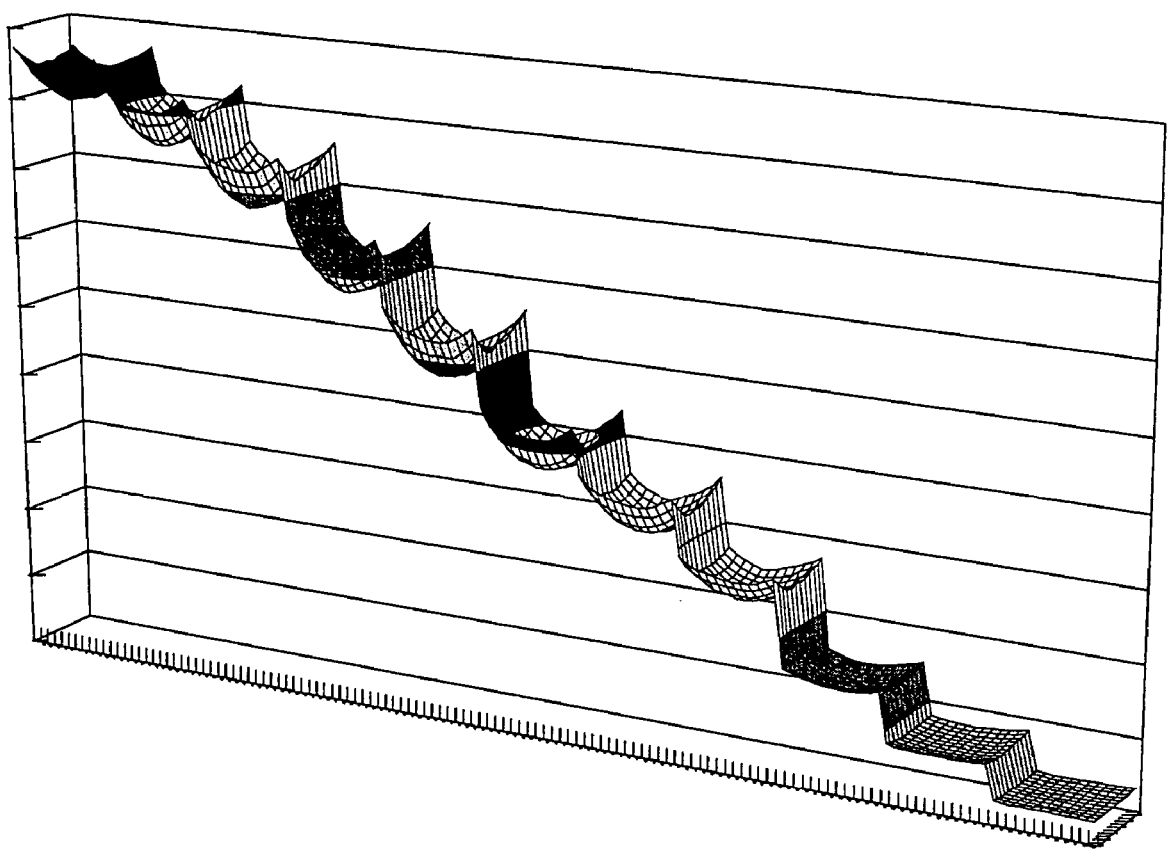
FIG. 17 shows the results of measurements carried out on standard plates having different reflection factors in the second embodiment together with the outputs of an area sensor.

FIG. 17 shows the results of measurements using those standard plates as the test piece 2 together with the output of the area sensor 8a. The axis of ordinates represents the output, and the axis of abscesses represents the respective standard plates that are successively aligned in a descending order in the reflection factor. Since the output data of each standard plate has not been subjected to light-irregularity correcting processes, it has a curved shape.

Figure 18:
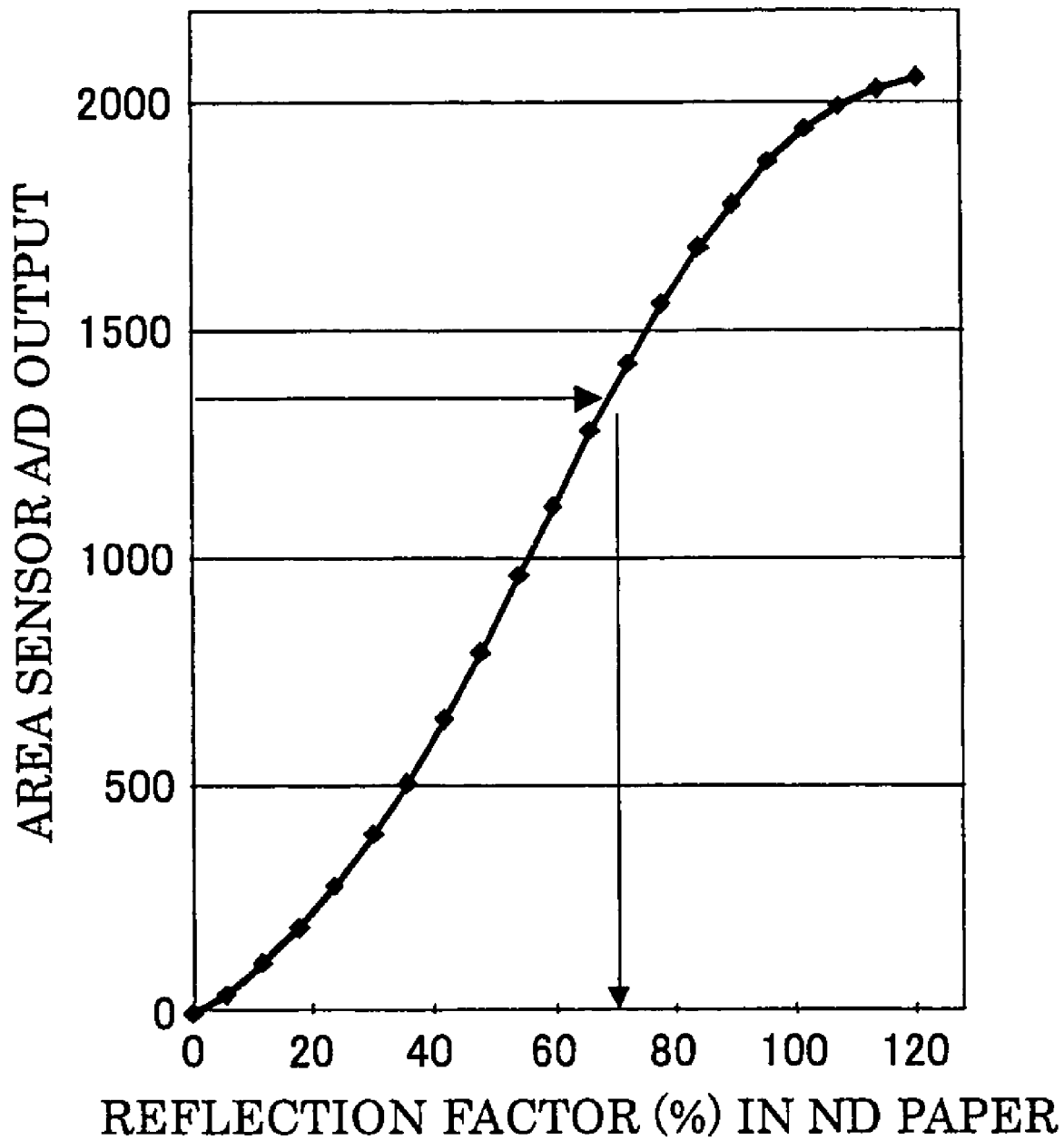
FIG. 18 is a drawing that shows the results of FIG. 17 with respect to one pixel of the image sensor.

FIG. 18 shows the relationship between the reflection factor and the output with respect to one pixel of the area sensor 8a. The axis of ordinates represents the output of the area sensor 8a, and the axis of abscissas represents known reflection factors of the standard plates. Since the output of the area sensor 8a has a non-linear property with respect to the quantity of received light, this curve exhibits an S-letter shape, which indicates the same characteristics as those shown in FIG. 5.

With respect to each pixel of the area sensor 8a, data as shown in FIG. 18 is stored as linearizing data for each pixel.

In the case when a sample whose reflection factor is unknown is measured, by using linearizing data for each of the pixels, the reflection factor is obtained from its output as shown by arrows in FIG. 18. The reflection factor is obtained by interpolating gaps between the actually measured points of the linearizing data.

The reflection factor of the unknown sample thus obtained is allowed to form reflection factor data in which irradiation irregularities due to a light source and non-linear properties of the lens and the area sensor 8a have been corrected, thereby preparing reflection-factor-related data having linearity.

Figure 19:
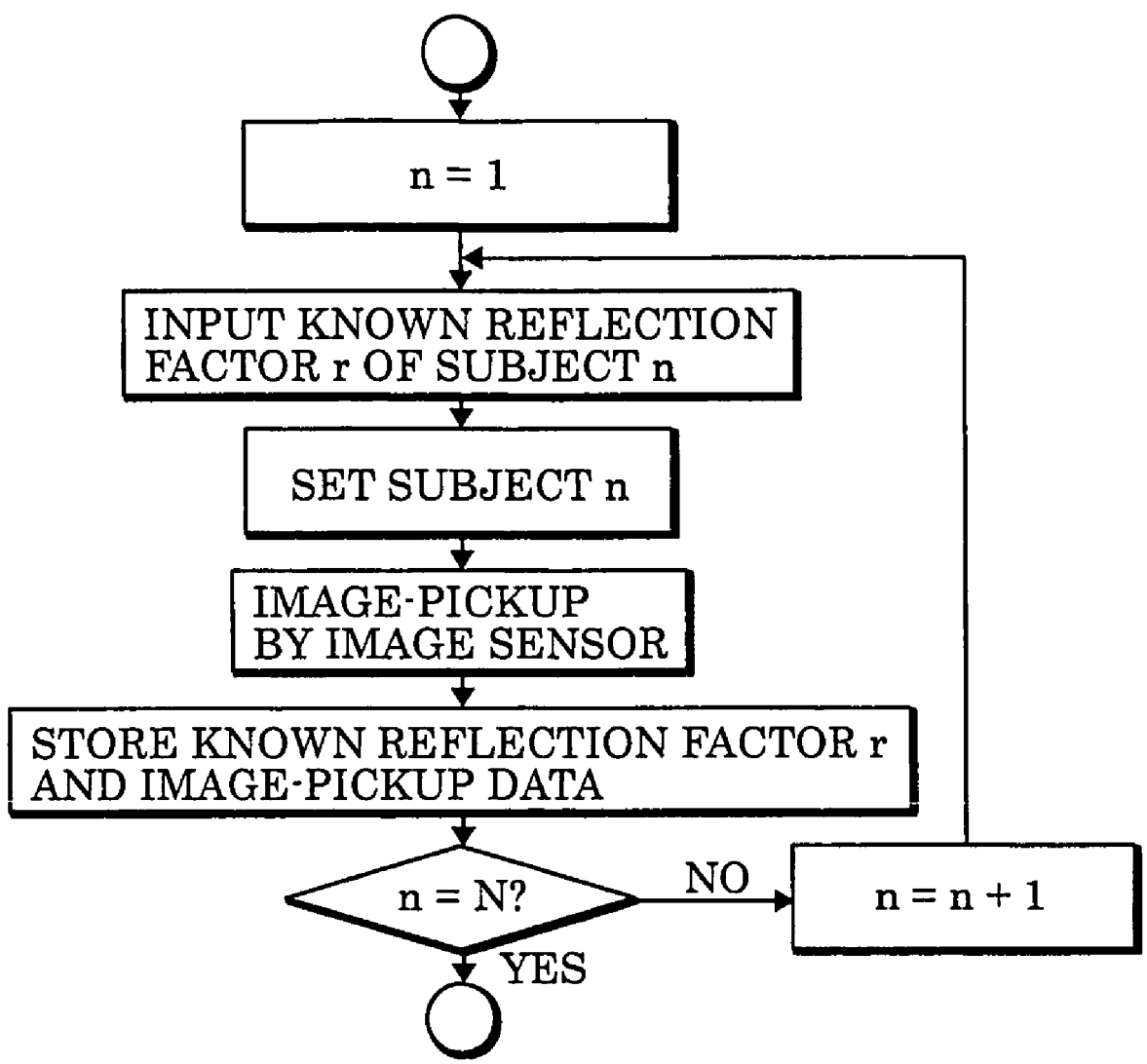
FIG. 19 is a flow chart that shows a sequence of processes to be carried out to obtain linearizing data in the second embodiment.
Figure 20:
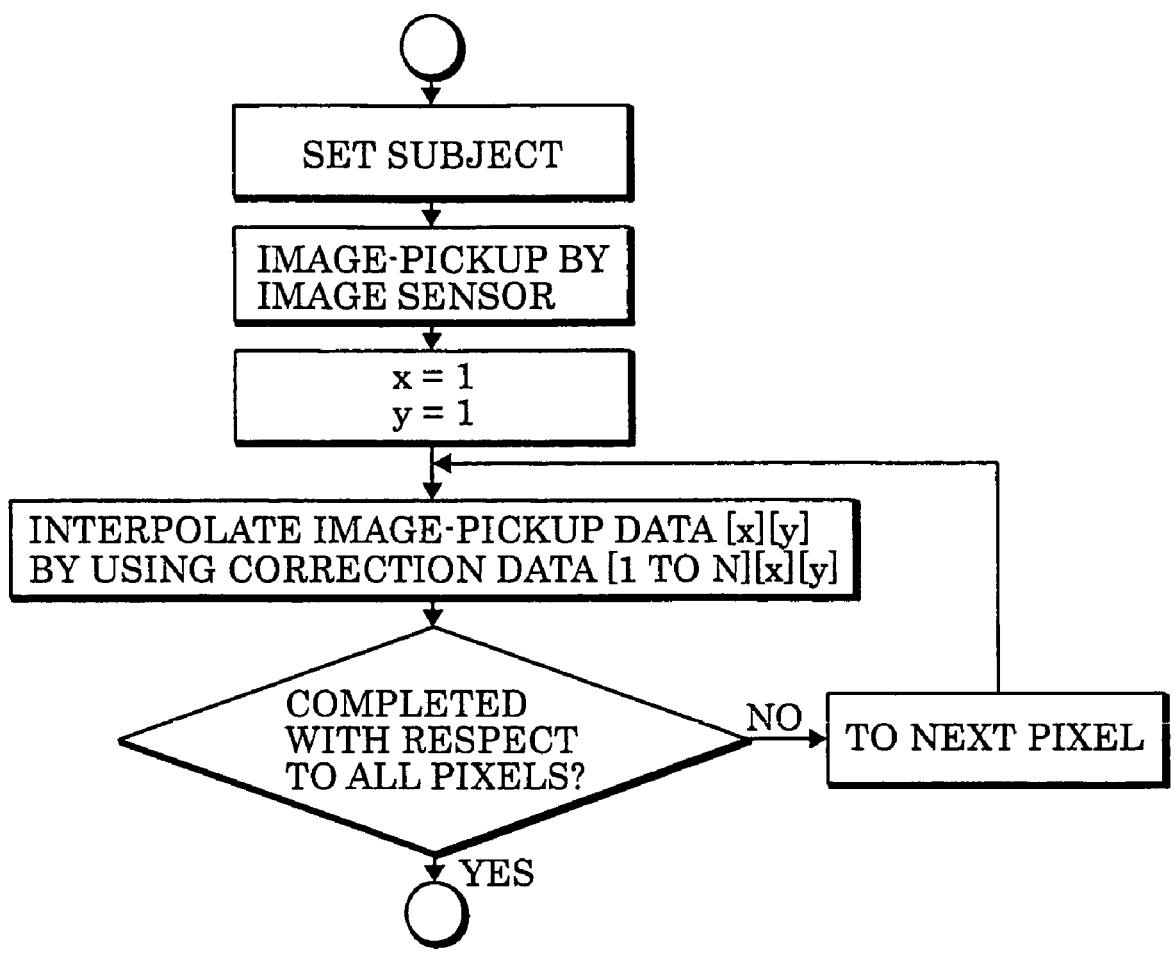
FIG. 20 is a flow chart that shows a sequence of reflection-factor measuring processes to be carried out on an unknown sample.

Referring to FIG. 19 and FIG. 20, the following description will further discuss these operations.

FIG. 19 shows a sequence used for obtaining linearizing data. Here, N-number of kinds of plates having different reflection factors are prepared as reference plates. In other words, 11 kinds that have varied reflection factors ranging from 100% to 0% on a 10% unit basis are prepared. One reference plate is placed at the position of the test piece 2, and an image thereof is picked up by the area sensor 8a. At this time, the known reflection factor r and image-pickup data of the reference plate are stored. These operations are repeated with respect to all the reference plates.

Thus, the linearizing data of FIG. 18 that indicates the relationship between the output and the reflection factor of each pixel of the image-pickup data is obtained for each of the pixels.

In the operations shown in FIG. 20, a sample whose reflection factor is unknown is placed at the position of the measuring object, and an image thereof is picked up by the area sensor 8a. Based upon the results of the picked up image, with respect to the coordinates (x, y) indicating the pixel position, the reflection factor is obtained from the output data of each pixel, in a manner as indicated by arrows in FIG. 16. These operations are carried out with respect to all the pixels.

EMBODIMENT 3

With respect to a third embodiment of a reflection-factor measuring device, the following description will discuss one example to which an output correction method in accordance with the third aspect of the present invention is applied.

Here, the optical system is the same as that shown in FIG. 16.

In this embodiment, the area sensor 8a is designed so that the exposing time during which the area sensor 8a receives light is programmable. With respect to such an image sensor, for example, a CMOS image sensor (H64283FP) made by Mitsubishi Electric Corporation, which is used in the embodiment shown in FIG. 3, may be used. However, not limited to CMOS image sensors, a CCD image sensor may be used as the area sensor 8a as long as it makes the exposing time programmable.

Although the output of the area sensor 8a does not have linearity with respect to the quantity of received light, the quantity of received light is directly proportional to the exposing time. Here, the quantity of received light is directly proportional to the reflection factor; therefore, even in the case of using a single reference plate, that is, a common reference plate, by changing the exposing time, it becomes possible to obtain the same results as the measurements using reference plates having different reflection factors.

A white plate serving as a reference plate is placed at the position of the measuring object 2 in FIG. 16. First, measurements are carried out by using reference exposing time. Next, while the white plate serving as the measuring object is maintained in the same state, the same measurements are carried out while the exposing time is reduced to 90% of the reference exposing time. In the same manner, the exposing time is reduced to 80%, 70% and so on.

Figure 21:
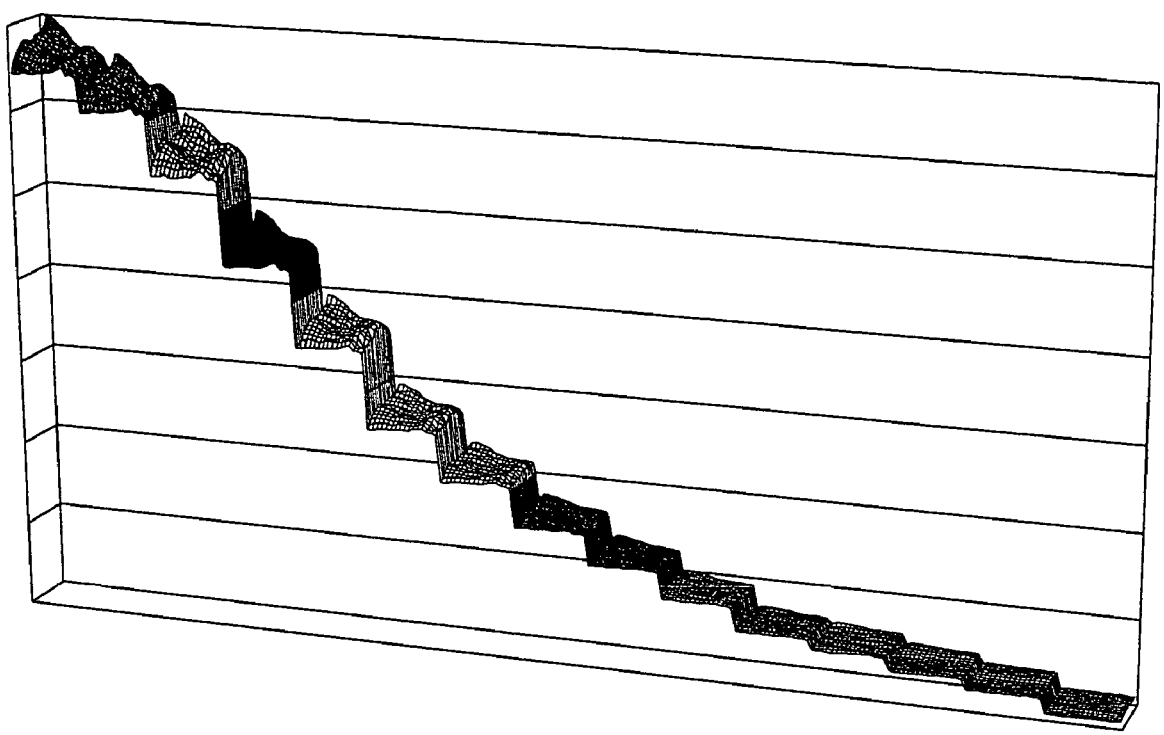
FIG. 21 is a drawing that shows the relationship between the output of the area sensor and the exposing time, obtained as the exposing time is reduced in a third embodiment of a reflection-factor measuring device.

FIG. 21 shows the relationship between the output (axis of ordinates) of the area sensor 8a and the exposing time (axis of abscissas, with the exposing time being shorter toward the right side) when the exposing time is reduced. In this case also, since no light-irregularity correction is carried out within the area sensor 8a, the output between pixels is varied.

Figure 22:
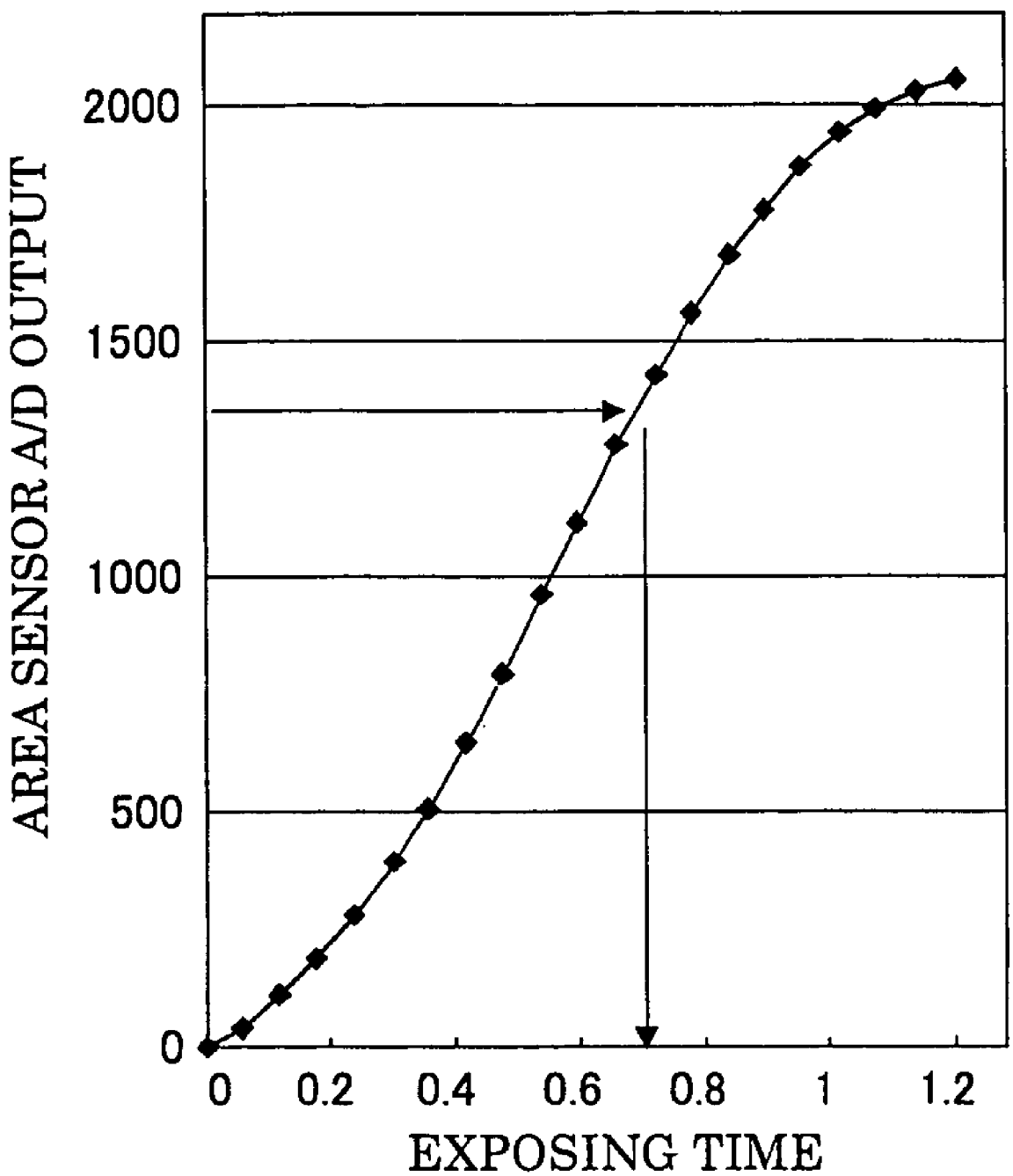
FIG. 22 is a drawing that shows the results of FIG. 21 with respect to one pixel of the image sensor.

FIG. 22 shows the relationship between the output and the exposing time with respect to each of the pixels, and the same results as those of FIG. 18 and FIG. 5 are obtained. The data shown in FIG. 22 is stored as linearizing data with respect to each of the pixels.

Figure 23:
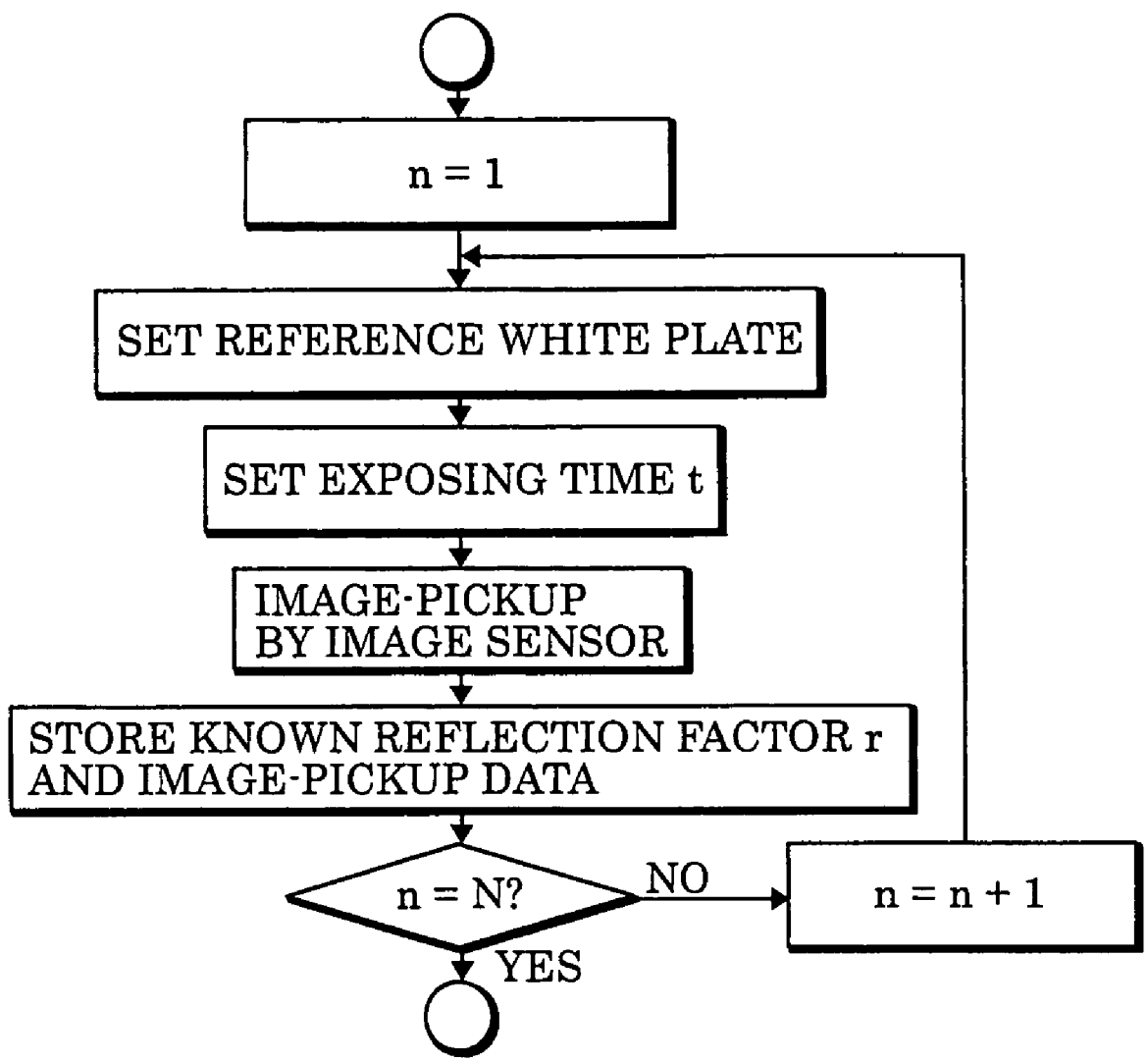
FIG. 23 is a flow chart that shows a sequence of processes carried out to obtain linearizing data in the third embodiment.

FIG. 23 shows the sequence for acquiring the linearizing data in a collective manner. The reference white plate is set as the measuring object 2, with the reference exposing time t being set. An image-pickup process is carried out by the area sensor 8a while light is applied during the corresponding exposing time so that the exposing time t and the image-pickup data are stored.

Next, the same measurements are repeated with the exposing time being reduced by 10%. In this manner, the measurements are repeatedly carried out with the exposing time being successively reduced; thus, the relationship between the sensor output and the exposing time with respect to each of the pixels is shown in FIG. 22. The exposing time on the axis of abscissas corresponds to the reflection factor.

Figure 24:
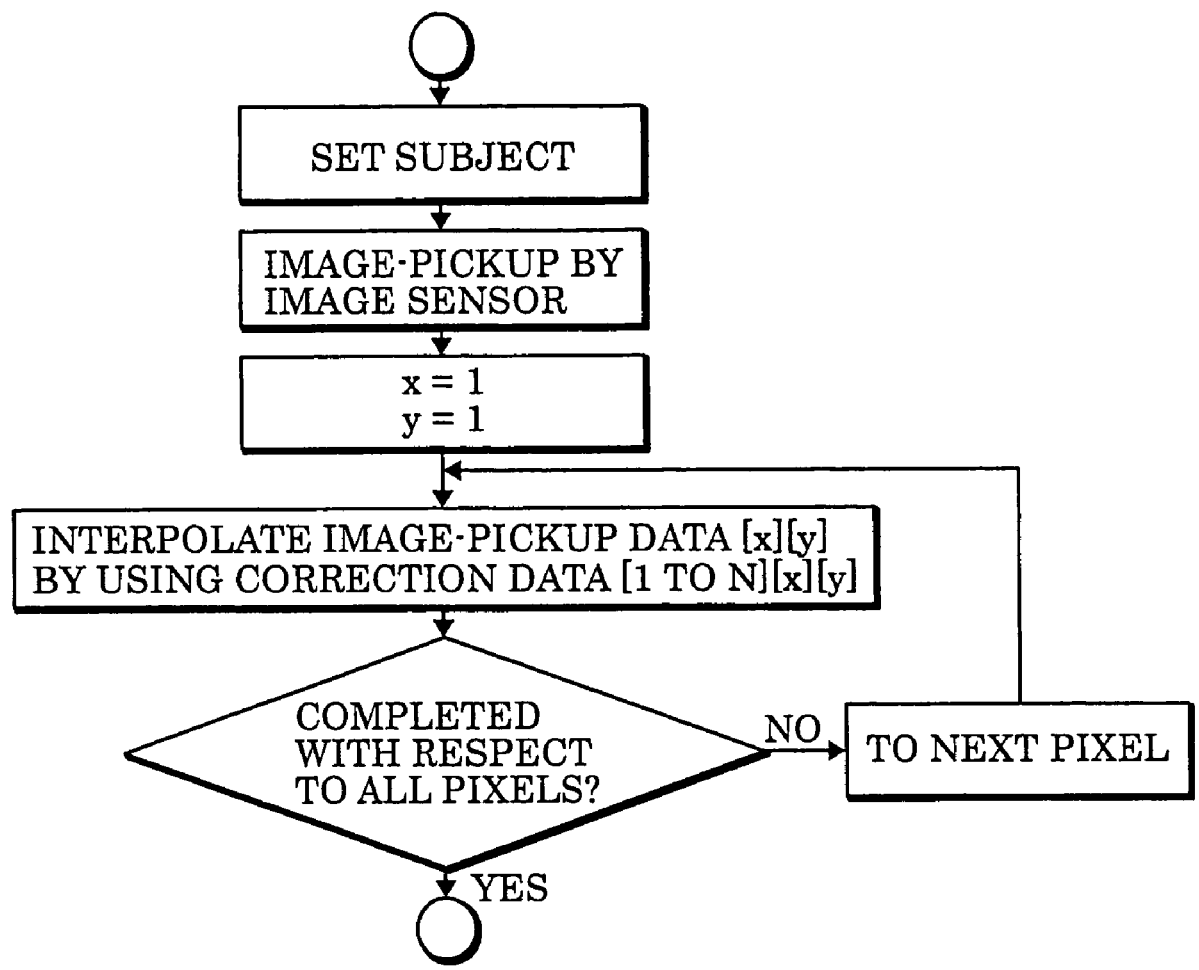
FIG. 24 is a flow chart that shows a sequence of reflection-factor measurements to be carried out on an unknown sample.

FIG. 24 shows a sequence of processes to be used for measuring a sample whose reflection factor is unknown, and this sequence is the same as that shown in FIG. 20. In this embodiment, the exposing time corresponding to the reflection factor is obtained with respect to each of the pixels.

Figure 25:
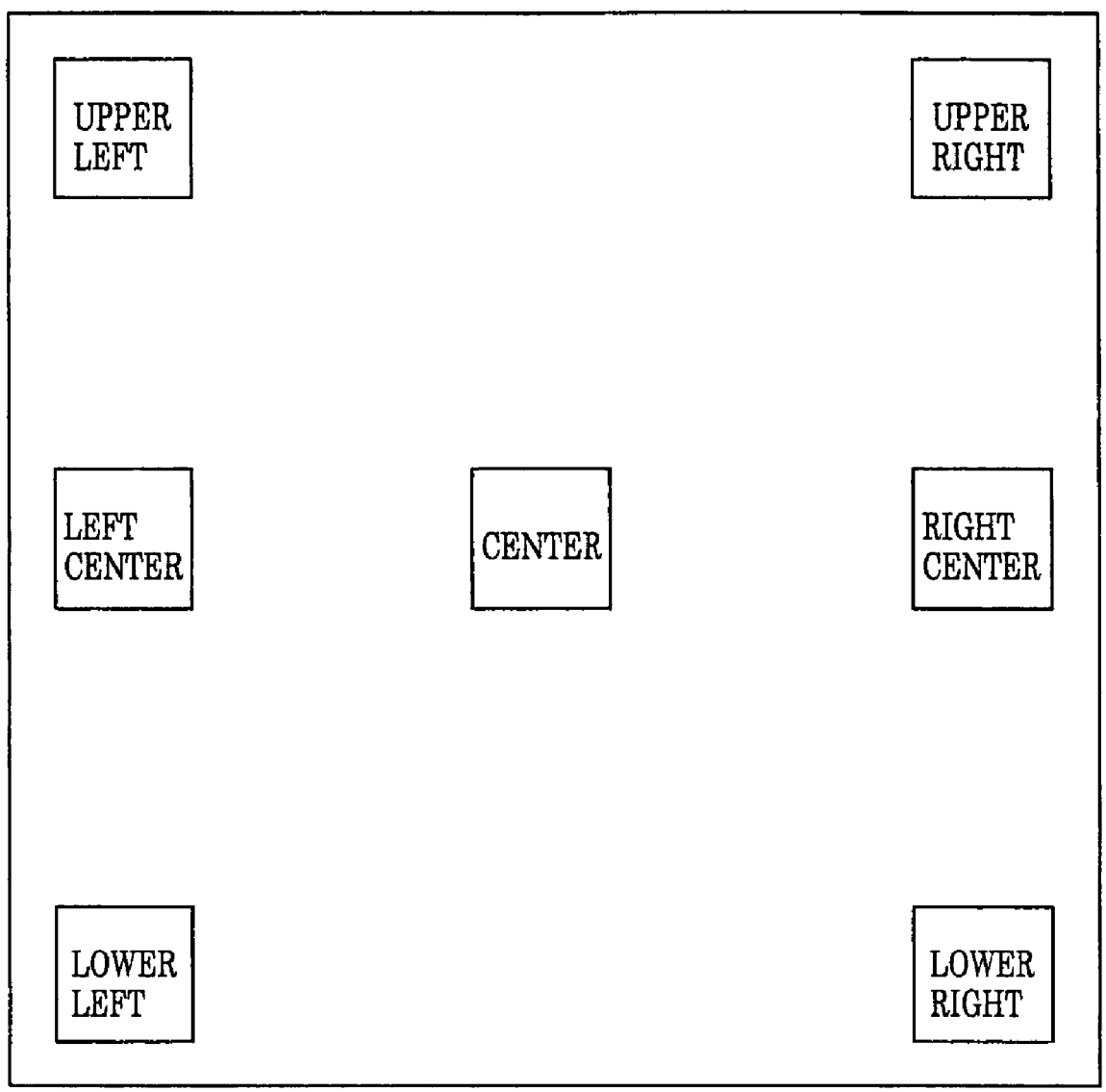
FIG. 25 is a plan view that shows data-acquiring pixel positions that are used for confirming data precision after correction in the third embodiment.
Figure 26:
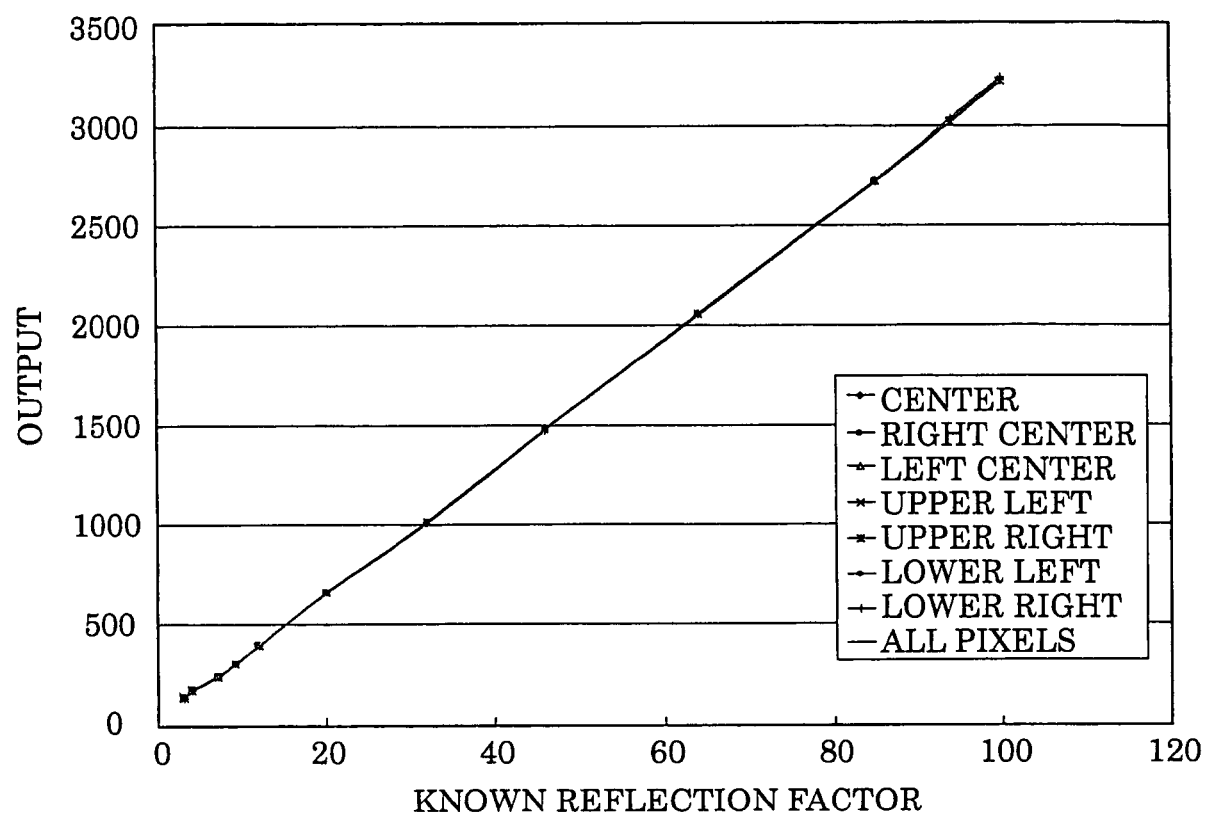
FIG. 26 is a graph that shows the relationship between the corrected output and reflection factor in respective pixels.

In this embodiment, data precision after the correction was confirmed. A plurality of image-pickup subjects, each having a known reflection factor, were measured. As shown in FIG. 25, pixels were selected at respective positions in the center portion and the peripheral portion of the area sensor 8a, and FIG. 26 shows the relationship between the corrected output and the reflection factor with respect to each of the pixels. The pixel output at each position may be an output from a single pixel or an average value of the outputs from some pixels in the vicinity of the position. The straight line represents the average value of all the pixels. In FIG. 26, the axis of abscissas represents the known reflection factor, and the axis of ordinates represents the corrected output.

The results shown in FIG. 26 indicate that irrespective of the pixel position within the area sensor 8a, it is possible to correct the non-linear property in the lens and the image sensor causing irradiation irregularities to a linear reflection factor-related value.

EMBODIMENT 4

In order to apply the reflection factor measuring device of the present invention to an immuno-chromatography analysis, measuring processes were carried out on the assumption of measurements to be applied to an immuno-chromatograph test piece. As shown in A to F of FIG. 27, six kinds of sample test pieces were prepared, which were formed by using a color ink-jet printer. The size of the sample test pieces was set to 10 mm×10 mm within the image-angle range.

These sample test pieces were acquired as images by the reflection factor measuring device of the present embodiment. FIG. 28 shows the picked-up image of E (think gradation) as a three-dimensional contour face graph among the 6 patterns of FIG. 27. The XY face was allowed to correspond to the plane of the sample test piece, the height (Z direction) was allowed to correspond to the reflection factor, and the contour face was formed by area-averaging 5×5 pixels. FIG. 28 shows that this reflection factor measuring device detects color-developing portions of the sample test piece with high fidelity.

Figure 27:
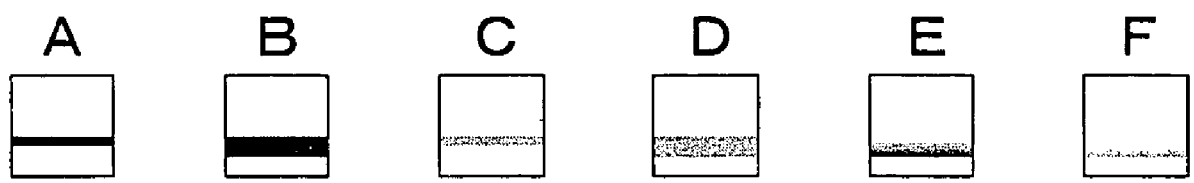
FIG. 27 shows patterns of a sample test paper.
Figure 28:
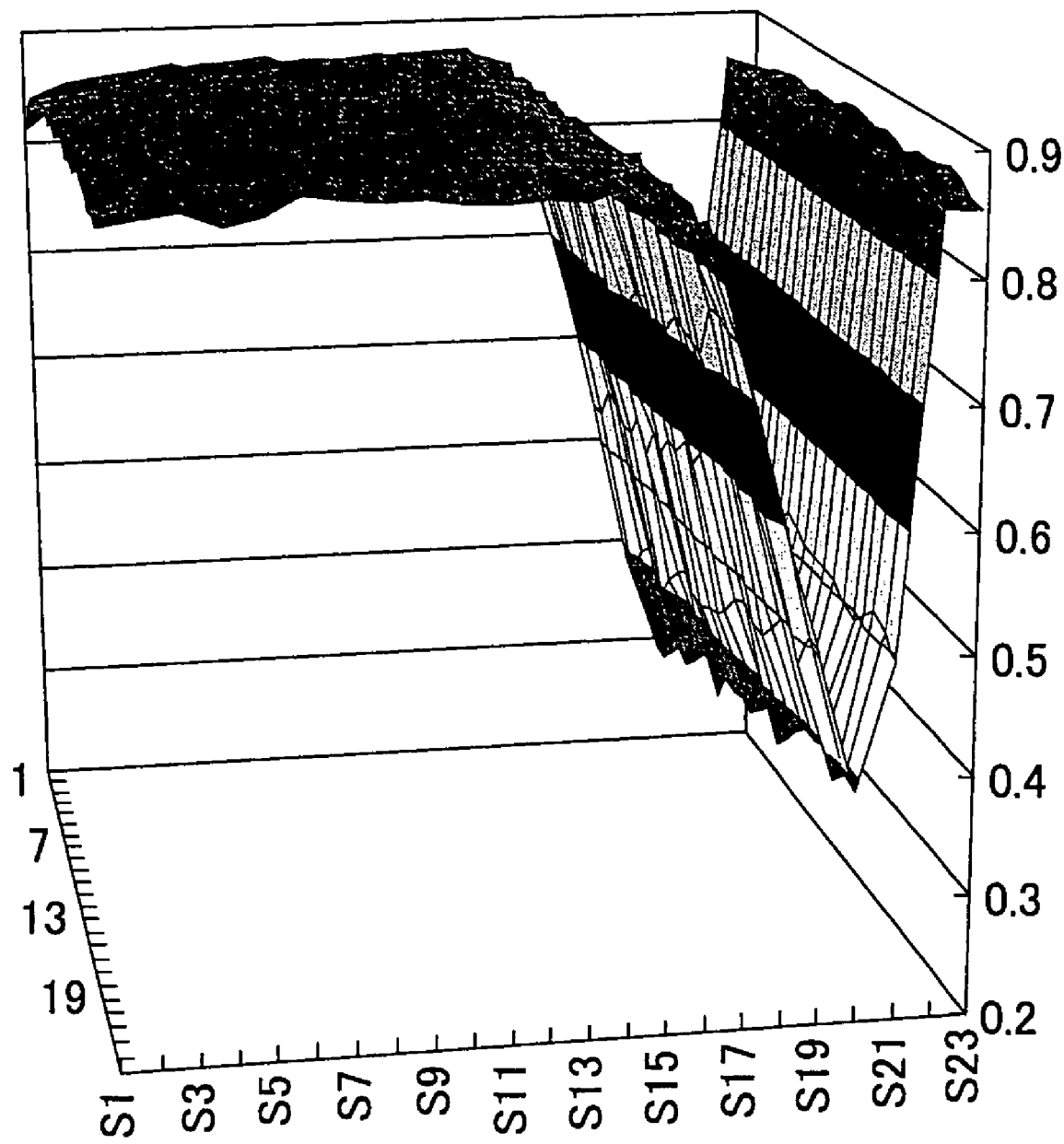
FIG. 28 shows a three-dimensional contour face graph obtained when a sample test paper having a pattern with a thin gradation is measured by the reflection-factor measuring device of the first embodiment.
Figure 29:
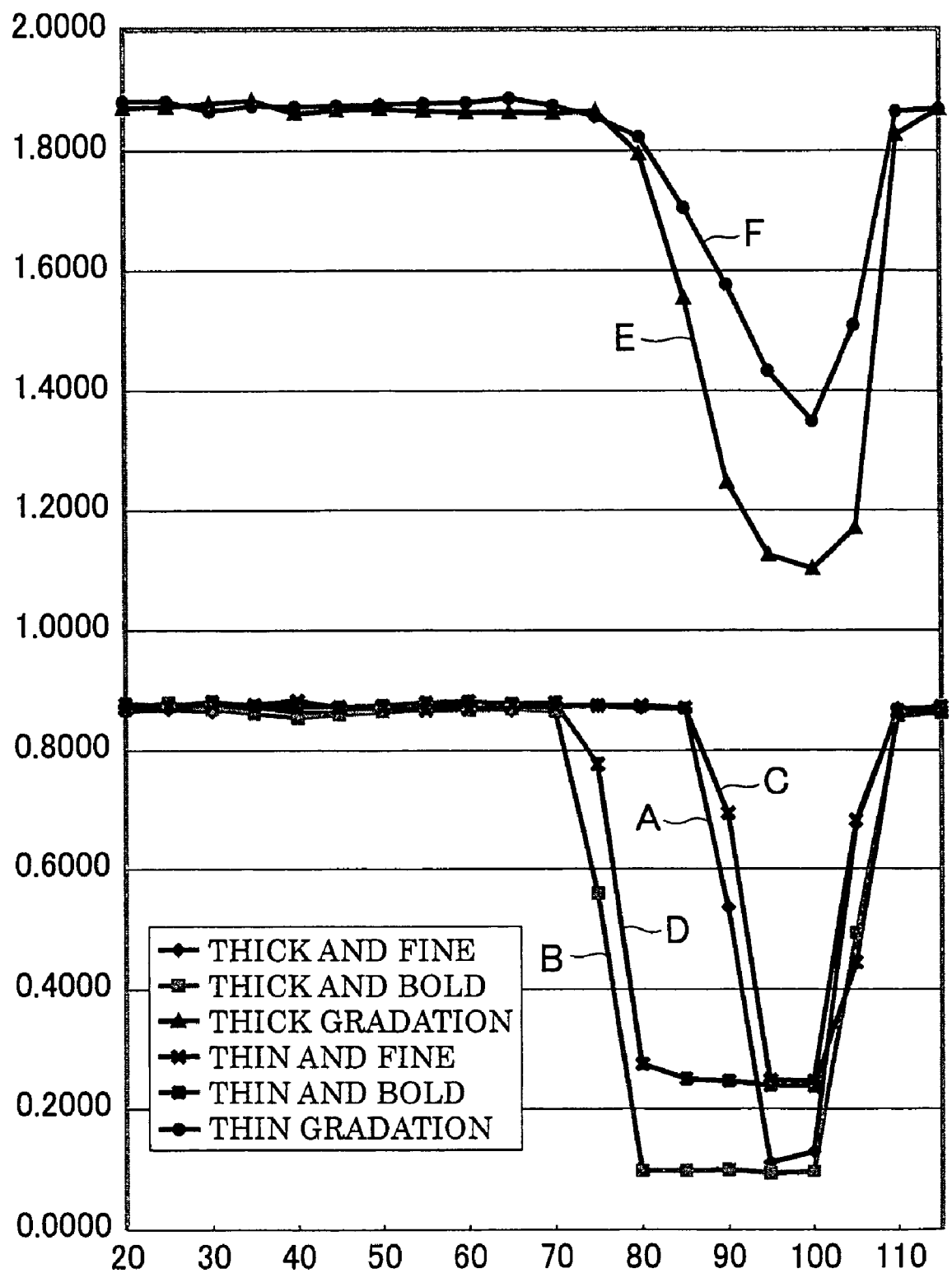
FIG. 29 is a drawing that shows the results of measurements carried out on the reflection factor of one line in the vicinity of the center of each sample test piece of six kinds by using the reflection-factor measuring device of the first embodiment.

FIG. 29 is a drawing in which images of the sample test pieces of 6 patterns of FIG. 27 are acquired by the reflection factor measuring device of the present embodiment so that a graph is formed with respect to one line in the vicinity of the center of each test piece. Symbols A to F in FIG. 29 correspond to symbols of 6 patterns of FIG. 27. The axis of ordinates represents the reflection factor, and for convenience of explanation, E and F are displayed in a shifted manner upward. The axis of abscesses represents measured positions on the line. FIG. 29 shows that the reflection factor measuring device reads features of color developing portions, such as thick, thin, bold and fine, of the sample test piece with high fidelity.

Therefore, it is found that the reaction amount (density) of the test piece can be quantified by volume-integrating a recessed portion of the contour face of FIG. 28, or area-integrating one line in the lateral direction as shown in FIG. 29.

Table 6 shows the results of the quantifying processes in the cases of thick and thin color-developing ranges with respect to a pair of test pieces of fine pattern and bold pattern respectively having the same density. Here, Σ represents the integral value.

sensor output measured by the reflection factor measuring device. The area sensor output is subjected to a pre-process in any one of methods disclosed in embodiments 1 to 3.

Figure 31A:
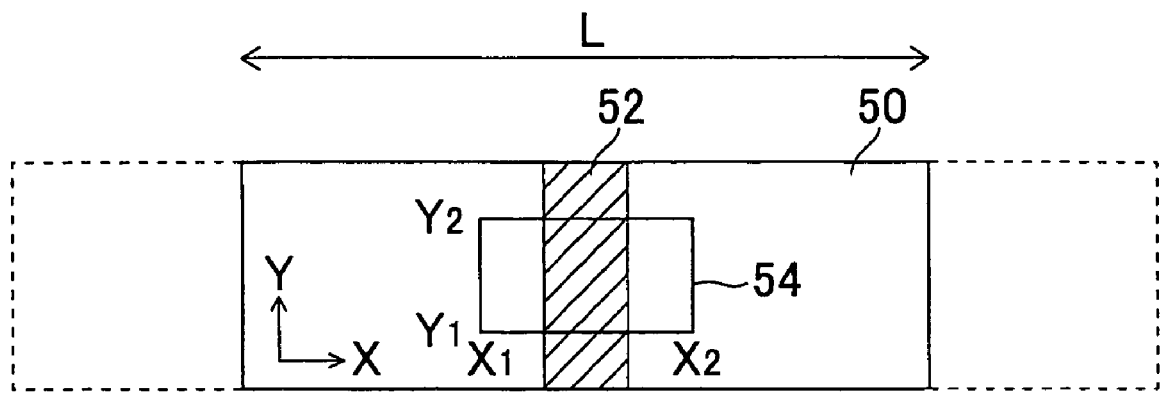
FIG. 31(A) is a plan view that shows an image picked up by the area sensor.
Figure 31B:
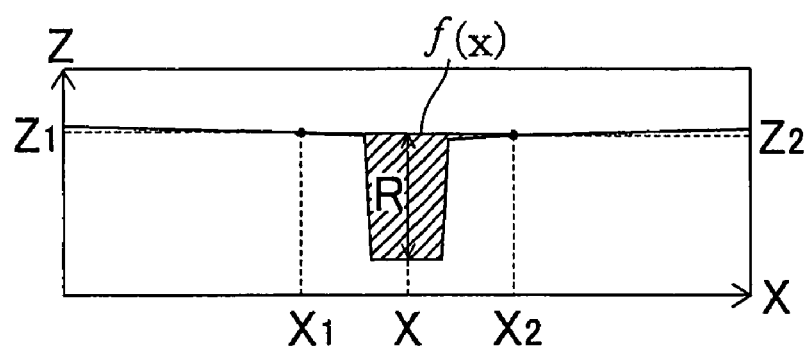
FIG. 31(B) is a drawing that shows the detection intensity along one X-axis with respect to the picked-up images.

FIG. 31(A) shows a picked-up image by the area sensor, and FIG. 31(B) indicates the detection intensity along one of the X-axes.

Reference numeral 50 denotes a test piece in which a portion (range indicated by L) indicated by a solid line in the center represents the range of the picked-up image by the area sensor. Reference numeral 52 indicates a color-developing area. Reference numeral 54 indicates a range in which an integral value of the refection factor is obtained, and an integration process is carried out with respect to the X-direction on an area that is greater than the color-developing area 52, and includes a non-color-developing area. With respect to each Y coordinate, integration processes are carried out on $X_1$ to $X_2$ with respect to the X coordinate, and then carried out on $Y_1$ to $Y_2$ with respect to the Y coordinate.

More specifically, these processes are carried out in the following manner. The two end points $X_1$ and $X_2$ of the range 54 that is area-specified in the X-axis direction with respect to each Y coordinate are connected by a straight line. Alternatively, two end points (also referred to as $X_1$ and $X_2$) that have the same level in intensity are found, and connected by a straight line. These two end points are located in a non-color developing area. This straight line is referred to as "baseline". With the Y-axis being fixed, suppose that the detection intensities at the two end coordinates $X_1$ and $X_2$ on the X-axis are set to $Z_1$ and $Z_2$. Then, the baseline f(X) is represented by the following equation:

$$f(X) = \{(Z_2-Z_1)/(X_2-X_1)\}(X-X_1) + Z_1$$

TABLE 6

| | WHITE AREA (15 × 68 pixel) | | | | ACTUAL AMOUNT OF COLORING | |
|---|---|---|---|---|---|---|
| | AVE | S.D. | C.V. (%) | COLORED AREA Σ | Σ | RATIO (%) |
| THIN AND FINE | 0.874 | 0.0072 | 0.82 | 870.52 (24 × 68 pixel) | 556.31 | 44.3 |
| THIN AND BOLD | 0.877 | 0.0072 | 0.82 | 1307.74 (48 × 68 pixel) | 1255.42 | 100.0 |
| THICK AND FINE | 0.870 | 0.0060 | 0.69 | 734.28 (24 × 68 pixel) | 685.08 | 44.1 |
| THICK AND BOLD | 0.867 | 0.0098 | 1.13 | 981.94 (48 × 68 pixel) | 1552.23 | 100.0 |

Table 6 shows that, in the respective densities, the value of bold color developing is virtually the same as the value of fine color developing.

Figure 30:
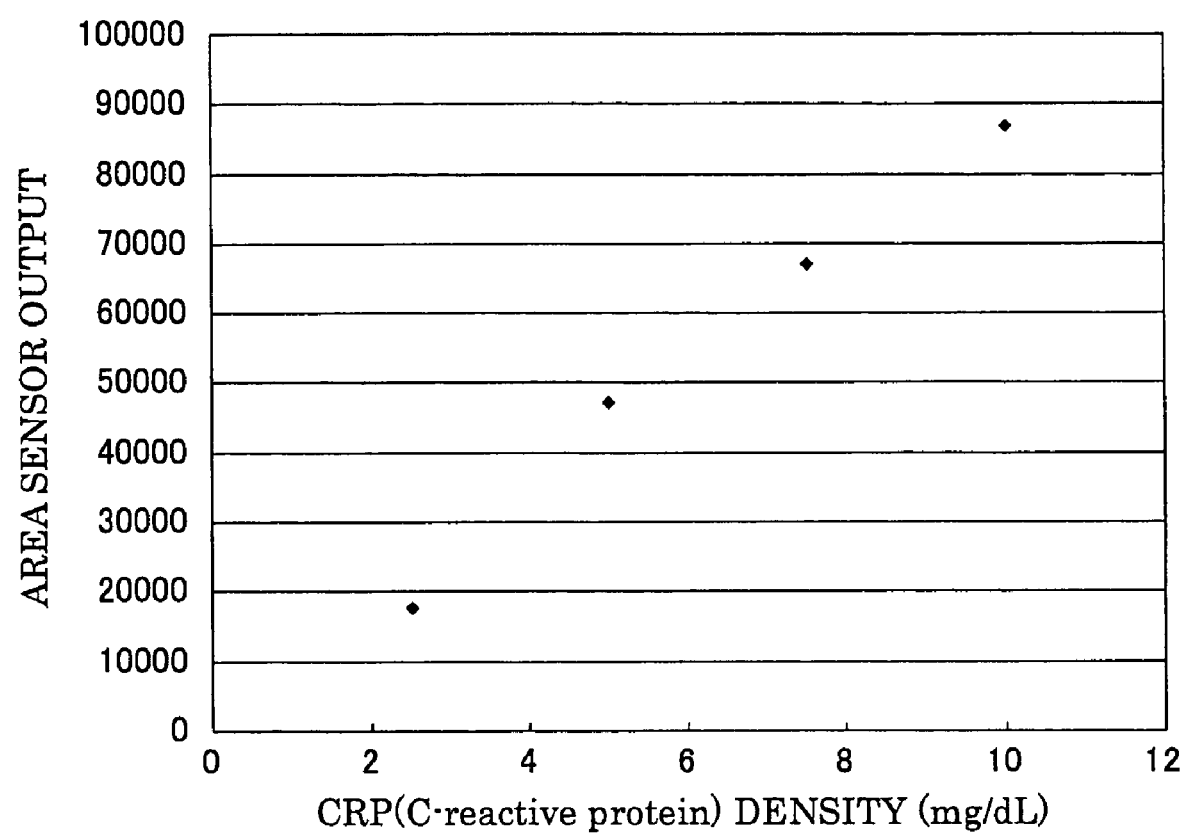
FIG. 30 is a drawing that shows a calibration curve obtained when the reflection-factor measuring device of the first embodiment measured CRP.

FIG. 30 shows an example in which the reflection factor measuring device of the first embodiment is applied as a measuring device for an actual immuno-chromatography analysis. The axis of abscissas represents the density of CRP (C-reactive protein: one of crystal proteins that extremely increases upon occurrence of inflammation), and the axis of ordinates represents the area sensor output obtained when color-developed immuno-chromatography test pieces that have color developments by the respective CRP densities are measured by the reflection factor measuring device of the present embodiment. This relationship is utilized as calibration-curve data to be used upon quantifying the sample density from the reflection factor in the present invention.

EMBODIMENT 5

The following description will discuss a preferred embodiment which is used for obtaining a reflection factor integral value of color developing portions from the area Suppose that the detection intensity of pixels (coordinates (X, Y)) on the same Y-axis is represented by Z. The value at the coordinates (X, Y) on the baseline is obtained from the above-mentioned equation f(X). This value is defined as the reference value REF. In other words, the reference value REF=f(X) holds. Since the reference value REF is also given as a function of Y coordinates, REF=f(X, Y) also holds.

The detection intensity Z at the coordinates (X, Y) is converted to the absorbing ratio r from the reference value REF. In other words, the following calculation is carried out:

$$r = 1 - (Z/REF)$$

When r is subjected to integration processes from $X_1$ to $X_2$, the integrated value V(Y) on the Y-axis is calculated.

This process for obtaining V(Y) is subjected to integration processes from $Y_1$ to $Y_2$ in the Y-axis detection range, the integrated value V in the area 54 is calculated.

The integrated value V thus calculated is converted into a quantitative numeric value such as a density value by using calibration curves stored in the measuring device.

Table 7 shows the results of the measurements on a test piece.

TABLE 7

| MEASURING No. | REFERENCE EXAMPLE | EXAMPLE |
|---|---|---|
| 1 | 1465 | 1997 |
| 2 | 1452 | 1977 |
| 3 | 1514 | 2003 |
| 4 | 1545 | 1994 |
| 5 | 1549 | 2008 |
| 6 | 1518 | 2006 |
| 7 | 1531 | 2037 |
| 8 | 1507 | 2021 |
| 9 | 1516 | 2006 |
| 10 | 1534 | 2030 |
| AVE. | 1513 | 2008 |
| Δ | 97 | 60 |
| S. D. | 31.9 | 17.7 |
| C. V. | 2.11% | 0.88% |

The column of "Example" in Table 7 shows the results of embodiment 5, and the column of "Reference example" shows the resulting integral values that have been calculated by setting the Z value at the non-color developing area on one end of the color developing area to the reference value REF. In any of calculations, measurements are carried out 10 times. Here, AVE. indicates the average value, Δ represents a difference between the maximum value and the minimum value in the area, S.D. indicated the standard deviation, and C.V. (%) represents a rate of change (standard deviation/average value). In this case, when comparisons are made among Δ, S.D. and C.V., the embodiment provides smaller values, that is, smaller deviations in the measured values, thereby indicating superior reproducibility.

INDUSTRIAL APPLICABILITY

The above-mentioned reflection factor measuring method, test-piece measuring method and device for achieving these methods can be applied to various fields, such as clinical inspections, food analyses and chemical analyses, as various analyzers, such as a dry chemistry analyzer like an immumo-chromatograph test-piece measuring device in which a test piece having a supporting member provided with a reagent portion.

What is claimed is:

1. A measuring method which receives light from a measuring object by using an image sensor, comprising
   a pre-process which comprises a linearizing correction process which corrects an output of each of pixels of the image sensor so as to make the output proportional to a quantity of incident light, and a light-irregularity correction process which corrects respective pixel outputs previously subjected to the linearizing correction process so that, upon measuring a reference object, the respective pixel outputs of the image sensor that have been previously subjected to the linearizing correction process are made even, and
   a calculating process which selects a color-developing area of the measuring object, and with respect to an area that is greater than the color-developing area at least in one direction, calculates an integral value of pixel outputs that have been subjected to the light-irregularity correction process.

2. The measuring method according to claim 1, wherein a reflection plate having even in-plane density or a blank is used as the reference object.

3. The measuring method according to claim 1, wherein, with respect to the calculation of the integral value, a straight line formed by correcting two points of pixel outputs sandwiching a color-developing area of the measuring object is set as a baseline value, and pixel outputs corresponding to respective positions of the measuring object are obtained based upon values obtained by converting the baseline value.

4. The measuring method according to claim 1, wherein the linearizing correction process comprises the following processes (A) and (B):
   (A) a process in which: a photodetector having linearity in an output thereof in response to the quantity of received light is arranged so that light to be made incident on the image sensor is simultaneously made incident on the photodetector, and upon variation in the quantity of incident light, the relationship between the image sensor output and the output of the photodetector is stored ad linearizing data; and
   (B) a process in which, upon measurement of a measuring object, the resulting image sensor output is corrected and made proportional to the output of the photodetector based upon the linearizing data.

5. The measuring method according to claim 4, wherein: the linearizing process is carried out by selecting some pixels in the vicinity of the brightest pixel within the image and using the average value of outputs of these pixels.

6. The measuring method according to claim 4, wherein the linearizing process is carried out on each of the pixels.

7. The measuring method according to claim 1, wherein the linearizing correction process comprises the following processed (A) and B:
   (A) a process in which: a plurality of standard plates having known reflection light rays that are respectively different from each other, and the relationship between the output from the image sensor output obtained when each of the standard plates is measured and the light from the reference plate is stored as linearizing data; and
   (B) a process in which, upon measurement of a measuring object, the resulting image sensor output is corrected and made proportional to the light ray from the standard plate based upon the linearizing data.

8. The measuring method according to claim 1, wherein the linearizing correction process comprises the following processes (A) and (B):
   (A) a process in which: the image sensor is allowed to variably set exposing time, and upon measuring one reference object, the relationship between each of image sensor outputs obtained from measurements carried out while changing the exposing time in a plurality of states and the corresponding exposing time is stored as linearizing data relating to light from the reference object, which is proportional to the exposing time, and
   (B) a process in which: the image sensor output, obtained upon measuring a measuring object, is corrected so as to be made proportional to light from the reference object that is obtained by the exposing time based upon the linearizing data.

9. The measuring method according to claim 1, wherein the light-irregularity correction process is carried out on image data by using a quantity of received light at a fixed ratio close to the saturated quantity of light with respect to the quantity of received light when the pixel has reached a saturated quantity of light.

10. A measuring method for a measuring object, wherein a sample density of the measuring object is calculated by applying calibration curve data that represents the relationship between the integral value and the sample density of the measuring object to the integral value that has been obtained by using any of methods disclosed in claim 1.

11. A measuring device, comprising:
an image sensor which receives light from a measuring object;
a linearizing correction data holding unit for holding linearizing correction data that is used for correcting the output of the image sensor from which an output when a quantity of received light is zero has been subtracted as dark data so as to be made proportional to the quantity of incident light;
a linearizing correction unit which carries out a linearizing correction process on the output of the image sensor based upon linearizing correction data stored in the linearizing correction data holding unit;
a light-irregularity correction data holding unit for holding light-irregularity correction data that is used for correcting outputs of respective pixels so that the respective pixel outputs of the image sensor that have been obtained upon measuring a reference object, and have been corrected by the linearizing correction data are evenly adjusted;
a light-irregularity correction unit which corrects light irregularities of the output of the image sensor on the basis of the light-irregularity correction data stored in the light-irregularity correction data holding unit, the output of the image sensor having been linearized; and
a calculation unit which selects a color-developing area of the measuring object by using respective pixel outputs of the image sensor, with respect to an area that is greater than the color-developing area at least in one direction, calculates an integral value of in-plane light from the measuring object,
wherein the calculation unit calculates the integral value of in-plane light from the measuring object by using the pixel outputs that have been subjected to the linearizing correction and the light-irregularity correction.

12. The measuring device according to claim 11, wherein: upon calculating the integral value, the calculation unit sets a straight line formed by connecting two points of pixel outputs sandwiching a color-developing area of the measuring object as a baseline value of the pixel outputs, and calculates the integral value on the basis of values obtained by converting pixel outputs corresponding to respective positions of the measuring object by using the baseline value.

13. The measuring device according to claim 12, wherein the calculation unit carries out an integration process on light from the measuring object with respect to an in-plane two-dimensional area of the measuring object.

14. The measuring device according to claim 12, wherein the calculation unit carries out an integration process on light from the measuring object with respect to an in-plane straight line of the measuring object.

15. The measuring device according to claim 11, further comprising a linearizing correction data forming unit which forms the linearizing correction data so as to allow the linearizing correction data holding unit to hold the resulting data.

16. The measuring device according to claim 15, wherein: a photodetector having linearity in an output thereof with respect to the quantity of received light is installed so that light to be made incident on the image sensor is simultaneously made incident on the photodetector, and the linearizing correction data forming unit generates the relationship between the image sensor output and the output of the photo detector obtained upon variation in the quantity of incident light onto the image sensor, as linearizing correction data.

17. The measuring device according to claim 16, wherein a photodiode is used as the photodetector having linearity in an output thereof with respect to the quantity of received light.

18. The measuring device according to claim 15, wherein the linearizing correction data forming unit generates the relationship between an image sensor output obtained upon measuring a plurality of standard plates which generate mutually different light rays that have been known and light from each of the standard plates, as the linearizing correction data.

19. The measuring device according to claim 15, wherein: the image sensor is allowed to variably set exposing time, and the linearizing correction data forming unit generates the relationship between an image sensor output obtained upon measuring one reference object while changing the exposing time in a plurality of stages and the corresponding exposing time as the linearizing correction data.

20. The measuring device according to claim 15, wherein the linearizing correction data forming unit forms linearizing correction data for each pixel.

21. The measuring device according to claim 15, wherein: the linearizing correction data forming unit measures a reference object and selects some pixels in the vicinity of the brightest pixel within an image so that the linearizing correction data is formed by using the average value of these pixel outputs.

22. The measuring device according to claim 11, further comprising: a light-irregularity correction data forming unit which forms light-irregularity correction data used for correcting respective pixel outputs so that the respective pixel outputs of the image sensor, which have been obtained upon measuring a flat plate having even in-plane density, and corrected by using the linearizing correction data, are made even, and allows the light-irregularity correction data holding unit to hold the resulting light-irregularity correction data.

23. The measuring device according to claim 22, wherein: the light-irregularity correction data forming unit measures a reference object, and forms light-irregularity correction data with respect to image data corresponding to the quantity of light having a fixed rate to the quantity of light when the pixel has reached the saturated quantity of light.

24. The measuring device according to claim 11, wherein a COD or CMOS sensor is used as the image sensor.

25. A measuring device for a measuring object, which is the measuring device disclosed in claim 11, further comprising:
a calibration-curve data holding unit which stores the relationship between an integral value of light from the measuring object and a sample density of the measuring object; and
a quantifying unit which applies the calibration curve data in the calibration-curve data holding unit to an integral value of light from the measuring object obtained by the calculation unit so as to calculate a sample density of the measuring object.

* * * * *